United States Patent
He et al.

(10) Patent No.: US 11,123,680 B1
(45) Date of Patent: Sep. 21, 2021

(54) DEVICES, SYSTEMS, AND METHODS FOR TREATING ETHYLENE OXIDE WASTE GAS

(71) Applicants: Chio Kang Medical, Inc., Palo Alto, CA (US); Qiaokang Biotech (Guangdong) Co., LTD., Guangzhou (CN)

(72) Inventors: Yecheng He, Guangzhou (CN); Dongxin Hou, Guangzhou (CN); Jianlong Xue, Guangzhou (CN); Guqun Ren, Guangzhou (CN); Xiuling Zhong, Guangzhou (CN); Xin Yin, Guangzhou (CN); Xuzhong Liao, Guangzhou (CN); Ziping Zhu, Guangzhou (CN); Qinghua Xiao, Guangzhou (CN); Yuhua Zou, Guangzhou (CN); Lixiong Feng, Palo Alto, CA (US)

(73) Assignees: Chio Kang Medical, Inc., Palo Alto, CA (US); Qiaokang Biotech (Guangdong) Co., LTD., Guangzhou (CN)

(*) Notice: Subject to any disclaimer, the term of this patent is extended or adjusted under 35 U.S.C. 154(b) by 0 days.

(21) Appl. No.: 17/002,540

(22) Filed: Aug. 25, 2020

Related U.S. Application Data

(63) Continuation of application No. PCT/CN2020/100119, filed on Jul. 3, 2020.

(30) Foreign Application Priority Data

Mar. 18, 2020 (CN) .......................... 202010190375.4
Mar. 18, 2020 (CN) .......................... 202020340598.X (Continued)

(51) Int. Cl.
   *B01D 53/053* (2006.01)
   *A61L 2/20* (2006.01)
   (Continued)

(52) U.S. Cl.
   CPC ....... *B01D 53/053* (2013.01); *B01D 53/0407* (2013.01); *B01D 53/047* (2013.01);
   (Continued)

(58) Field of Classification Search
   CPC  B01D 53/0407; B01D 53/047; B01D 53/053; B01D 53/0438; B01D 53/0446;
   (Continued)

(56) References Cited

U.S. PATENT DOCUMENTS 1,954,056 A * 4/1934 Miller ................ B01D 53/0438
                                                    62/143
2,586,670 A * 2/1952 Lambertsen ....... B01D 53/0446
                                                    96/149

(Continued)

FOREIGN PATENT DOCUMENTS

| CN | 1223166 A | 7/1999 |
|---|---|---|
| CN | 1397474 A | 2/2003 |

(Continued)

OTHER PUBLICATIONS

CN210088451U_ENG (Espacenet machine translation of Zheng) (Year: 2020).*

(Continued)

*Primary Examiner* — Jonathan Miller
*Assistant Examiner* — Gabriel E Gitman
(74) *Attorney, Agent, or Firm* — Adsero IP

(57) ABSTRACT

The present disclosure discloses a device, system, and method for treating an ethylene oxide waste gas. The system includes a first pressure swing adsorption tower, a first thermostatic assembly, a gas storage tank, a first branch pipe, (Continued)

and a second branch pipe. The first pressure swing adsorption tower comprises a first accommodating chamber which accommodates an adsorption material. A first vent port and a first exhaust port are in communication with the first accommodating chamber. The first pressure swing adsorption tower is partially disposed in the first thermostatic assembly. The gas storage tank comprises a gas inlet/outlet port. The first branch pipe and the second branch pipe are in communication with the first vent port. The first branch pipe couples the first vent port with the gas inlet/outlet port and the second branch pipe introduces an ethylene oxide waste gas into the first pressure swing adsorption tower.

9 Claims, 10 Drawing Sheets

(30) Foreign Application Priority Data

| Mar. 18, 2020 | (CN) | ................ 202020340779.2 |
| Mar. 18, 2020 | (CN) | ................ CN202010190355.7 |
| Mar. 19, 2020 | (CN) | ................ 202010194457.6 |
| Mar. 19, 2020 | (CN) | ................ 202020348776.3 |

(51) Int. Cl.
- B01D 53/04 (2006.01)
- B01D 53/75 (2006.01)
- B01D 53/78 (2006.01)
- B01D 53/047 (2006.01)
- A61L 2/26 (2006.01)

(52) U.S. Cl.
CPC ..... *B01D 53/0438* (2013.01); *B01D 53/0446* (2013.01); *B01D 53/75* (2013.01); *B01D 53/78* (2013.01); *A61L 2/206* (2013.01); *A61L 2/26* (2013.01); *B01D 2257/708* (2013.01); *B01D 2258/02* (2013.01); *B01D 2259/402* (2013.01); *B01D 2259/4146* (2013.01)

(58) Field of Classification Search
CPC .. B01D 53/75; B01D 53/78; B01D 2259/402; B01D 2257/708; B01D 2258/02; B01D 2259/4146; A61L 2/206; A61L 2/26
See application file for complete search history.

(56) References Cited

U.S. PATENT DOCUMENTS

| 2,817,689 | A |   | 12/1957 | White |
| 3,022,054 | A |   | 2/1962 | Kotzebue |
| 3,572,391 | A |   | 3/1971 | Hirsch et al. |
| 3,598,543 | A | * | 8/1971 | Crosby .................. F01N 3/2832 |
|   |   |   |   | 422/175 |
| 3,844,739 | A | * | 10/1974 | Alfrey, Jr. .............. B01D 53/04 |
|   |   |   |   | 95/146 |
| 3,961,920 | A |   | 6/1976 | Gilbert |
| 3,997,633 | A |   | 12/1976 | Leva et al. |
| 4,112,054 | A |   | 9/1978 | Feingold et al. |
| 4,119,539 | A |   | 10/1978 | Ettel et al. |
| 4,134,425 | A |   | 1/1979 | Gussefeld et al. |
| 4,243,636 | A |   | 1/1981 | Shiraki et al. |
| 4,301,113 | A |   | 11/1981 | Alguire et al. |
| 4,517,167 | A |   | 5/1985 | Popescu et al. |
| 4,549,363 | A |   | 10/1985 | Buonicore |
| 4,555,251 | A |   | 11/1985 | Jonsson |
| 4,831,196 | A |   | 5/1989 | Buonicore et al. |
| 5,084,075 | A | * | 1/1992 | Sircar .................. B01D 53/0476 |
|   |   |   |   | 95/26 |
| 5,204,075 | A |   | 4/1993 | Jain et al. |
| 5,270,000 | A |   | 12/1993 | Goldner et al. |
| 5,283,035 | A | * | 2/1994 | Karthaus ................ A61L 2/206 |
|   |   |   |   | 422/31 |
| 5,290,345 | A |   | 3/1994 | Osendorf et al. |
| 5,511,409 | A |   | 4/1996 | Knaebel |
| 5,522,808 | A | * | 6/1996 | Skalla .................... A61B 18/00 |
|   |   |   |   | 604/317 |
| 5,607,652 | A |   | 3/1997 | Hellmuth et al. |
| 5,641,455 | A |   | 6/1997 | Rosenlund et al. |
| 5,702,669 | A |   | 12/1997 | Green |
| 5,741,470 | A | * | 4/1998 | Wenzler ................. B01D 53/72 |
|   |   |   |   | 423/245.1 |
| 5,755,857 | A |   | 5/1998 | Acharya et al. |
| 5,779,773 | A |   | 7/1998 | Cam et al. |
| 5,964,927 | A |   | 10/1999 | Graham et al. |
| 6,156,101 | A | * | 12/2000 | Naheiri ................. B01D 53/053 |
|   |   |   |   | 95/101 |
| 6,684,648 | B2 |   | 2/2004 | Faqih |
| 6,743,402 | B2 |   | 6/2004 | Shimakawa |
| 7,316,733 | B1 |   | 1/2008 | Hedrick |
| 7,625,535 | B2 |   | 12/2009 | Yamaguchi |
| 8,110,156 | B2 |   | 2/2012 | Ricciardi et al. |
| 8,431,085 | B2 |   | 4/2013 | Froderberg et al. |
| 9,616,143 | B2 |   | 4/2017 | Snyder et al. |
| 10,987,443 | B1 |   | 4/2021 | Hu et al. |
| 2002/0046569 | A1 |   | 4/2002 | Faqih |
| 2002/0197194 | A1 |   | 12/2002 | Machado et al. |
| 2005/0145108 | A1 |   | 7/2005 | Rubin |
| 2006/0236860 | A1 | * | 10/2006 | Sumida ................. B01D 53/047 |
|   |   |   |   | 95/96 |
| 2006/0249027 | A1 |   | 11/2006 | Adolphsen et al. |
| 2007/0209383 | A1 |   | 9/2007 | Hutton |
| 2008/0078289 | A1 |   | 4/2008 | Sergi et al. |
| 2008/0080999 | A1 |   | 4/2008 | Bondar |
| 2008/0289591 | A1 | * | 11/2008 | Tessier .................. F17C 11/007 |
|   |   |   |   | 123/41.31 |
| 2010/0196194 | A1 |   | 8/2010 | Voeten et al. |
| 2011/0265644 | A1 | * | 11/2011 | Swami ................. C01B 13/0251 |
|   |   |   |   | 95/22 |
| 2011/0283885 | A1 |   | 11/2011 | Thiele |
| 2012/0031268 | A1 | * | 2/2012 | Yaghi .................... C07D 301/32 |
|   |   |   |   | 95/96 |
| 2012/0298207 | A1 |   | 11/2012 | Woelk et al. |
| 2014/0119989 | A1 |   | 5/2014 | Hayashi |
| 2014/0251130 | A1 | * | 9/2014 | Sprinkle ............... B01D 53/053 |
|   |   |   |   | 95/22 |
| 2014/0290162 | A1 |   | 10/2014 | Tanimoto |
| 2016/0010883 | A1 |   | 1/2016 | Jomitz et al. |
| 2017/0056813 | A1 |   | 3/2017 | McMahon et al. |
| 2019/0076776 | A1 |   | 3/2019 | Mahecha-Botero et al. |
| 2019/0151791 | A1 |   | 5/2019 | Awadh et al. |
| 2019/0175971 | A1 |   | 6/2019 | Moore et al. |
| 2020/0148655 | A1 |   | 5/2020 | Duff et al. |

FOREIGN PATENT DOCUMENTS

| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103908688 A | 7/2014 |
| CN | 203749877 U | 8/2014 |
| CN | 203750388 U | 8/2014 |
| CN | 203750389 U | 8/2014 |

(56) References Cited

FOREIGN PATENT DOCUMENTS

| | | |
|---|---|---|
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 105132060 A | 12/2015 |
| CN | 105327665 A | 2/2016 |
| CN | 105664822 A | 2/2016 |
| CN | 205300112 U | 6/2016 |
| CN | 210721130 U | 6/2016 |
| CN | 106139199 A | 11/2016 |
| CN | 106421844 A | 2/2017 |
| CN | 106475021 A | 3/2017 |
| CN | 106582126 A | 4/2017 |
| CN | 206443946 U | 8/2017 |
| CN | 206535551 U | 10/2017 |
| CN | 206853397 U | 1/2018 |
| CN | 107677016 A | 2/2018 |
| CN | 207169397 U | 4/2018 |
| CN | 207187436 U | 4/2018 |
| CN | 207356290 U | 5/2018 |
| CN | 207745676 U | 8/2018 |
| CN | 207913454 U | 9/2018 |
| CN | 108607511 A | 10/2018 |
| CN | 208047841 U | 11/2018 |
| CN | 208218734 U | 12/2018 |
| CN | 109382064 A | 2/2019 |
| CN | 208448985 U | 2/2019 |
| CN | 208893903 U | 5/2019 |
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U  *  2/2020  ............ B01D 53/02 |||
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| JP | 2013172790 A | 10/2016 |
| JP | 2010259648 A | 5/2018 |
| WO | WO2011002277 A1 | 1/2011 |
| WO | WO-2019-136504 A1 | 7/2019 |
| WO | WO2019236249 A1 | 12/2019 |

OTHER PUBLICATIONS

International Application No. PCT/CN2020/101140 as prepared by the Chinese International Searching Authority filed on Jul. 9, 2020, 59 pages.

U.S. Appl. No. 17/012,857, TrackOne Bypass CON Application filed Sep. 4, 2020, 148 pages.

International Application No. PCT/CN2020/100143 as prepared by the Chinese International Searching Authority filed on Jul. 3, 2020, 25 pages.

U.S. Appl. No. 17/002,500, TrackOne Bypass CON Application filed Aug. 25, 2020, 61 pages.

International Application No. PCT/CN2020/100125 as prepared by the Chinese International Searching Authority filed on Jul. 3, 2020, 27 pages.

U.S. Appl. No. 17/002,523, TrackOne Bypass CON Application filed Aug. 25, 2020, 72 pages.

U.S. Appl. No. 17/002,523 Non-Final Office Action, dated Oct. 27, 2020, 54 pages.

International Application No. PCT/CN2020/100115 as prepared by the Chinese International Searching Authority filed on Jul. 3, 2020, 22 pages.

U.S. Appl. No. 17/002,529, TrackOne Bypass CON Application filed Aug. 25, 2020, 64 pages.

International Application No. PCT/CN2020/100119 as prepared by the Chinese International Searching Authority filed on Jul. 3, 2020, 29 pages.

International Application No. PCT/CN2020/100120 as prepared by the Chinese International Searching Authority filed on Jul. 3, 2020, 28 pages.

U.S. Appl. No. 17/004,730, TrackOne Bypass CON Application filed Aug. 27, 2020, 77 pages.

International Application No. PCT/CN2020/101142 as prepared by the Chinese International Searching Authority filed on Jul. 9, 2020, 29 pages.

U.S. Appl. No. 17/012,864, TrackOne Bypass CON Application filed Sep. 4, 2020, 78 pages.

International Application No. PCT/CN2020/100144 as prepared by the Chinese International Searching Authority filed on Jul. 3, 2020, 24 pages.

U.S. Appl. No. 17/004,903, TrackOne Bypass CON Application filed Aug. 27, 2020, 67 pages.

U.S. Appl. No. 17/004,903 Notice of Allowance, dated Nov. 6, 2020, 19 pages.

International Application No. PCT/CN2020/100122 as prepared by the Chinese International Searching Authority filed on Jul. 3, 2020, 34 pages.

U.S. Appl. No. 17/004,930, TrackOne Bypass CON Application filed Aug. 27, 2020, 80 pages.

U.S. Appl. No. 17/004,930 Office Action-Restriction Requirement, dated Nov. 4, 2020, 6 pages.

International Application No. PCT/CN2020/100113 as prepared by the Chinese International Searching Authority filed on Jul. 3, 2020, 35 pages.

U.S. Appl. No. 17/004,971, TrackOne Bypass CON Application filed Aug. 27, 2020, 75 pages.

U.S. Appl. No. 17/012,857, Non-Final Office Action, dated Nov. 24, 2020, 13 pages.

U.S. Appl. No. 17/002,500, Non-Final Office Action dated Dec. 8, 2020, 109 pages.

Kahm et al., 2018 "Lyapunov exponents with Model Predictive Control for exothermic batch reactors" IFAC-PapersOnline, 51, 417-422.

U.S. Appl. No. 17/004,971, Office Action-Restriction Requirement, dated Dec. 9, 2020, 6 pages.

U.S. Appl. No. 17/002,523 Notice of Allowance, dated Dec. 17, 2020, 35 pages.

U.S. Appl. No. 17/004,930 Office Action-Restriction Requirement, dated Dec. 18, 2020, 8 pages.

U.S. Appl. No. 17/004,930 Non-Final Office Action dated Jan. 26, 2021, 28 pages.

International Search Report and Written Opinion, International Application No. PCT/CN2020/101140 dated Dec. 21, 2020, 11 pages.

International Search Report and Written Opinion, International Application No. PCT/CN2020/100143 dated Dec. 21, 2020, 9 pages.

International Search Report and Written Opinion, International Application No. PCT/CN2020/100125 dated Dec. 23, 2020, 9 pages.

International Search Report and Written Opinion, International Application No. PCT/CN2020/100115 dated Dec. 16, 2020, 11 pages.

International Search Report and Written Opinion, International Application No. PCT/CN2020/100119 dated Dec. 17, 2020, 9 pages.

International Search Report and Written Opinion, International Application No. PCT/CN2020/101142 dated Dec. 16, 2020, 11 pages.

International Search Report and Written Opinion, International Application No. PCT/CN2020/100144 dated Dec. 18, 2020, 10 pages.

U.S. Appl. No. 17/002,500, Final Office Action dated Feb. 8, 2021, 57 pages.

(56) References Cited

OTHER PUBLICATIONS

U.S. Appl. No. 17/004,971, Notice of Allowance, dated Feb. 8, 2021, 30 pages.
U.S. Appl. No. 17/002,529, Non-Final Office Action-Restriction Requirement dated Feb. 17, 2021, 11 pages.
U.S. Appl. No. 17/012,857, Notice of Allowance, dated Mar. 1, 2021, 26 pages.
U.S. Appl. No. 17/002,540, Final Office Action, dated Mar. 26, 2021, 36 pages.
U.S. Appl. No. 17/004,730, Non-Final Office Action, dated Apr. 1, 2021, 30 pages.
U.S. Appl. No. 17/002,500, Non-Final Office Action dated Apr. 14, 2021, 89 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.
U.S. Appl. No. 17/004,930 Notice of Allowance, dated Apr. 28, 2020, 35 pages.
U.S. Appl. No. 17/004,903 Notice of Allowance, dated May 17, 2021, 20 pages.
U.S. Appl. No. 17/002,529 Notice of Allowance, dated May 3, 2021, 30 pages.
U.S. Appl. No. 17/002,523 Notice of Allowance, dated May 27, 2021, 26 pages.
U.S. Appl. No. 17/012,864, Notice of Allowance, dated Jun. 15, 2021, 56 pages.
U.S. Appl. No. 17/004,730, Notice of Allowance, dated Jun. 24, 2021, 30 pages.
U.S. Appl. No. 17/012,857, Notice of Allowance, dated Jun. 28, 2021, 21 pages.
U.S. Appl. No. 17/002,500, Notice of Allowance mailed on Jul. 8, 2021, 27 pages.

\* cited by examiner

DEVICES, SYSTEMS, AND METHODS FOR TREATING ETHYLENE OXIDE WASTE GAS

CROSS-REFERENCE TO RELATED APPLICATION

This application is a continuation of International Application No. PCT/CN2020/100119, filed on Jul. 3, 2020, which claims the benefit of Chinese Patent Application No. CN202010190355.7, filed on Mar. 18, 2020, Chinese Patent Application No. CN202020340779.2, filed on Mar. 18, 2020, Chinese Patent Application No. CN202010190375.4, filed on Mar. 18, 2020, Chinese Patent Application No. CN202020340598.X, filed on Mar. 18, 2020, Chinese Patent Application No. 202010194457.6, filed on Mar. 19, 2020, and Chinese Patent Application No. CN202020348776.3, filed on Mar. 19, 2020, the entire contents of each of which are incorporated herein by reference in their entireties for all purposes.

TECHNICAL FIELD

The present disclosure relates to the technical field of waste gas treatment, and more particularly relates to devices, systems, and methods for treating an ethylene oxide waste gas.

BACKGROUND

Ethylene oxide ("EO") is a broad-spectrum, high-efficiency sterilization agent with excellent sterilization performance. The ethylene oxide has strong penetrating power and is able to kill various microorganisms at room temperature, without damaging the sterilized articles during sterilization. The sterilization method using ethylene oxide gas is currently one of the most prominent low-temperature sterilization methods and is most commonly used in hospitals.

However, ethylene oxide itself is toxic, flammable, and explosive, and after sterilization is performed by using ethylene oxide gas, the sterilization waste gas generated in a sterilizer needs to be treated before discharge. Currently, methods for treating the ethylene oxide waste gas include: (1) Catalytic combustion method in which the sterilization waste gas is combusted into a non-toxic substance by catalytic combustion, however, this method has potential safety hazards during the treatment of the sterilization waste gas, since ethylene oxide is flammable and explosive; (2) Adsorption method in which the sterilization waste gas is catalyzed by acid to produce ethylene glycol, which is suitable for the treatment of the high-concentration ethylene oxide waste gas, but may cause secondary pollution if the treatment is not performed properly; and (3) Low temperature recovery method in which the sterilization waste gas is condensed at −29° C. to recover the ethylene oxide, however, this method has high energy consumption and has very high requirements for equipment.

Hence, there is a need for more robust and scalable solutions for implementing waste gas treatment, and, more particularly, for implementing systems, devices, and methods for treating ethylene oxide waste gas.

SUMMARY

In view of this, the present disclosure provides devices, systems, and methods for treating an ethylene oxide waste gas.

A device/system for treating an ethylene oxide waste gas might include: a first pressure swing adsorption tower comprising a first accommodating chamber configured to accommodate a first adsorption material, the first pressure swing absorption tower further comprising a first vent port and a first exhaust port in communication with the first accommodating chamber; a first thermostatic assembly, the first pressure swing adsorption tower being at least partially disposed in the first thermostatic assembly; a gas storage tank comprising a gas inlet/outlet port; and a first branch pipe and a second branch pipe. The first branch pipe and the second branch pipe are in communication with the first vent port. The first branch pipe couples the first vent port with the gas inlet/outlet port, and the second branch pipe is configured to introduce the ethylene oxide waste gas into the first pressure swing adsorption tower through the first vent port.

In the device/system for treating the ethylene oxide waste gas, the ethylene oxide in the ethylene oxide waste gas is adsorbed and recovered by the adsorption material in the first pressure swing adsorption tower, which has good recovery effect, safe and simple operation, and has no environmental pollution. Meanwhile, the adsorption material in the pressure swing adsorption tower can be desorbed and regenerated under specific temperature and pressure conditions, which is conducive to the recovery and reuse of ethylene oxide on the one hand, and is also conducive to the regeneration and reuse of the adsorption material on the other hand.

One embodiment of the present disclosure further provides a system for treating an ethylene oxide waste gas, which includes an ethylene oxide sterilizer and the aforementioned device/system for treating the ethylene oxide waste gas. The first vent port is configured to be in communication with an exhaust port of the ethylene oxide sterilizer.

The aforementioned system for treating the ethylene oxide waste gas includes the aforementioned device/system for treating the ethylene oxide waste gas, and therefore has the technical effects of the device for treating the ethylene oxide waste gas, that is, has good recovery effect for ethylene oxide, safe and simple operation, and has no environmental pollution.

One embodiment of the present disclosure further provides a method for treating an ethylene oxide waste gas performed by the aforementioned device/system for treating the ethylene oxide waste gas, including the following steps: S1, injecting the ethylene oxide waste gas into the first pressure swing adsorption tower; S2, simultaneously cooling the first pressure swing adsorption tower to a first preset temperature by the first thermostatic assembly while increasing a pressure in the first pressure swing adsorption tower to a first preset pressure, and adsorbing ethylene oxide in the ethylene oxide waste gas by the adsorption material in the first pressure swing adsorption tower; S3, stopping cooling of the first pressure swing adsorption tower by the first thermostatic assembly, causing the first pressure swing adsorption tower to be in communication with an outside of the first pressure swing adsorption tower through the first exhaust port, and discharging gas in the first pressure swing adsorption tower through the first exhaust port, so as to reduce the pressure in the first pressure swing adsorption tower to a second preset pressure; and S4, isolating the first exhaust port from the outside of the first pressure swing adsorption tower, causing the first vent port to be in communication with the gas inlet/outlet port, and desorbing the ethylene oxide adsorbed by the adsorption material in the first pressure swing adsorption tower to enter the gas storage tank through the first vent port and the gas inlet/outlet port, so as to reduce the pressure in the first pressure swing adsorption tower to a third preset pressure.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Examples of the disclosure are described below with more details with reference to the accompanying drawings. It should be understood, however, that the examples are exemplary and should not be construed as limiting the scope of the present disclosure. Rather, these examples are provided so that this disclosure will be thorough and complete, and will fully convey the scope of the disclosure to those skilled in the art.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

It will be understood that an element, when being referred to as being "fixed," "coupled," or "connected" to another element, may be directly fixed, coupled or connected to the other element or via an intermediate element. Such terms as "vertical," "horizontal," "left," "right" and the like used herein are for illustrative purposes only and should not be construed as limiting the implementation of the present disclosure.

Unless otherwise defined, all terms herein, including technical and scientific terms, shall have the same meaning as commonly accepted by a person skilled in the art to which this disclosure belongs. Such terms, as used herein, are for the purpose of describing exemplary examples of, and without limiting, the present disclosure. The term "and/or" as used herein refers to any and all combinations of one or more items recited.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
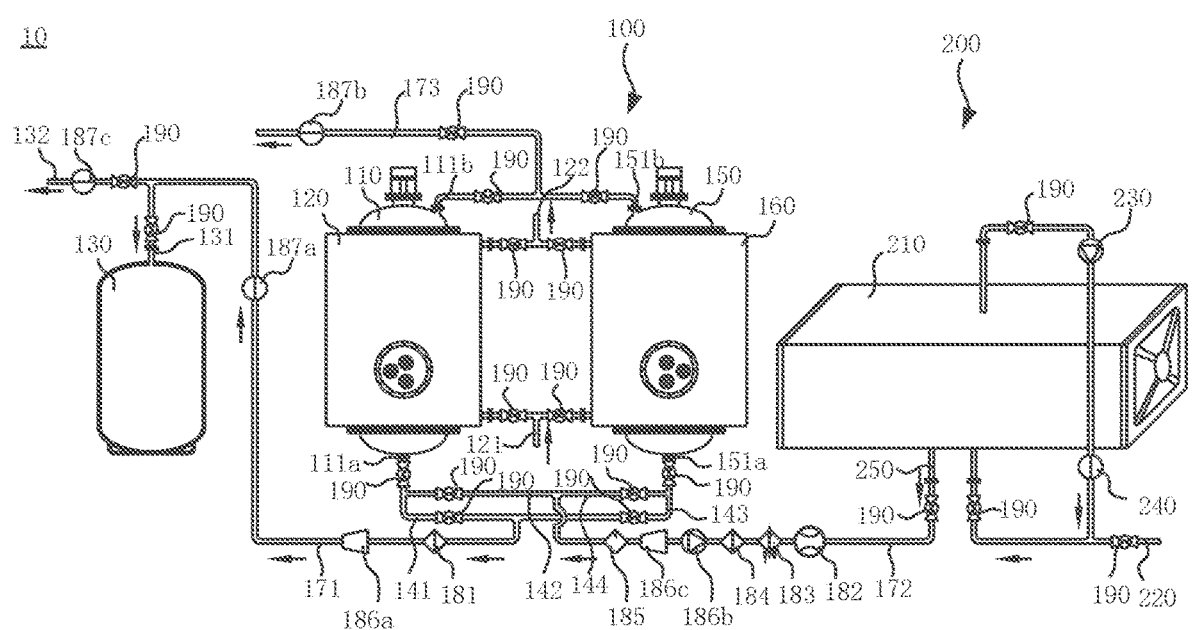
FIG. 1 is a schematic structural diagram of a device/system for treating an ethylene oxide waste gas according to an embodiment of the present disclosure.

As shown in FIG. 1, an embodiment of the present disclosure provides a system 10 for treating an ethylene oxide waste gas including a device/system 100 for treating the ethylene oxide waste gas and an ethylene oxide sterilizer 200. The system 10 for treating the ethylene oxide waste gas has a good recovery effect for ethylene oxide, safe and simple operation, and does not cause pollution to the environment.

The following numbering is set forth to define the elements/components/devices of system 10: 10: system for treating ethylene oxide waste gas, 100: device/system for treating ethylene oxide waste gas, 110: first pressure swing adsorption tower, 111a: first vent port, 111b: first exhaust port, 111c: first accommodating chamber, 112: first tower body, 113a: first upper sealing cover, 113b: first lower sealing cover, 114a: water-absorbing material, 114b: oil-absorbing material, 114c: adsorption material, 115: primary gas distributor, 115a: first hole, 116: secondary gas distributor, 116a: second hole, 117: lower mesh plate, 117a: third hole, 118: first filler compression assembly, 118a: filler compression grid, 118b: filler compression column, 118c: fourth hole, 119a: sealing gasket, 119b: flange, 119c: observation hole, 120: first thermostatic assembly, 121: water inlet port, 122: water outlet port, 130: gas storage tank, 131: gas inlet/outlet port, 132: exhaust pipe, 141: first branch pipe, 142: second branch pipe, 143: third branch pipe, 144: fourth branch pipe, 150: second pressure swing adsorption tower, 151a: second vent port, 151b: second exhaust port, 160: second thermostatic assembly, 171: first main pipe, 172: second main pipe, 173: discharge pipe, 181: gas filter, 182: flowmeter, 183: heat exchanger, 184: gas-liquid separator, 185: gas dryer, 186a: first booster pump, 186b: first vacuum pump, 186c: second booster pump, 187a: first ethylene oxide concentration detector, 187b: second ethylene oxide concentration detector, 187c: third ethylene oxide concentration detector, 190: valve, 200: ethylene oxide sterilizer, 210: sterilizer body, 220: gas inlet pipe, 230: second vacuum pump, 240: fourth ethylene oxide concentration detector, and 250: fourth exhaust port.

Specifically, the device/system 100 for treating the ethylene oxide waste gas may include a first pressure swing adsorption tower 110, a first thermostatic assembly 120, a gas storage tank 130, a first branch pipe 141, and a second branch pipe 142. In a further embodiment, the device/system 100 may further include a second pressure swing adsorption tower 150, a second thermostatic assembly 160, a third branch pipe 143, and a fourth branch pipe 144. The pressure swing adsorption tower is also called PSA tower.

Figure 2:
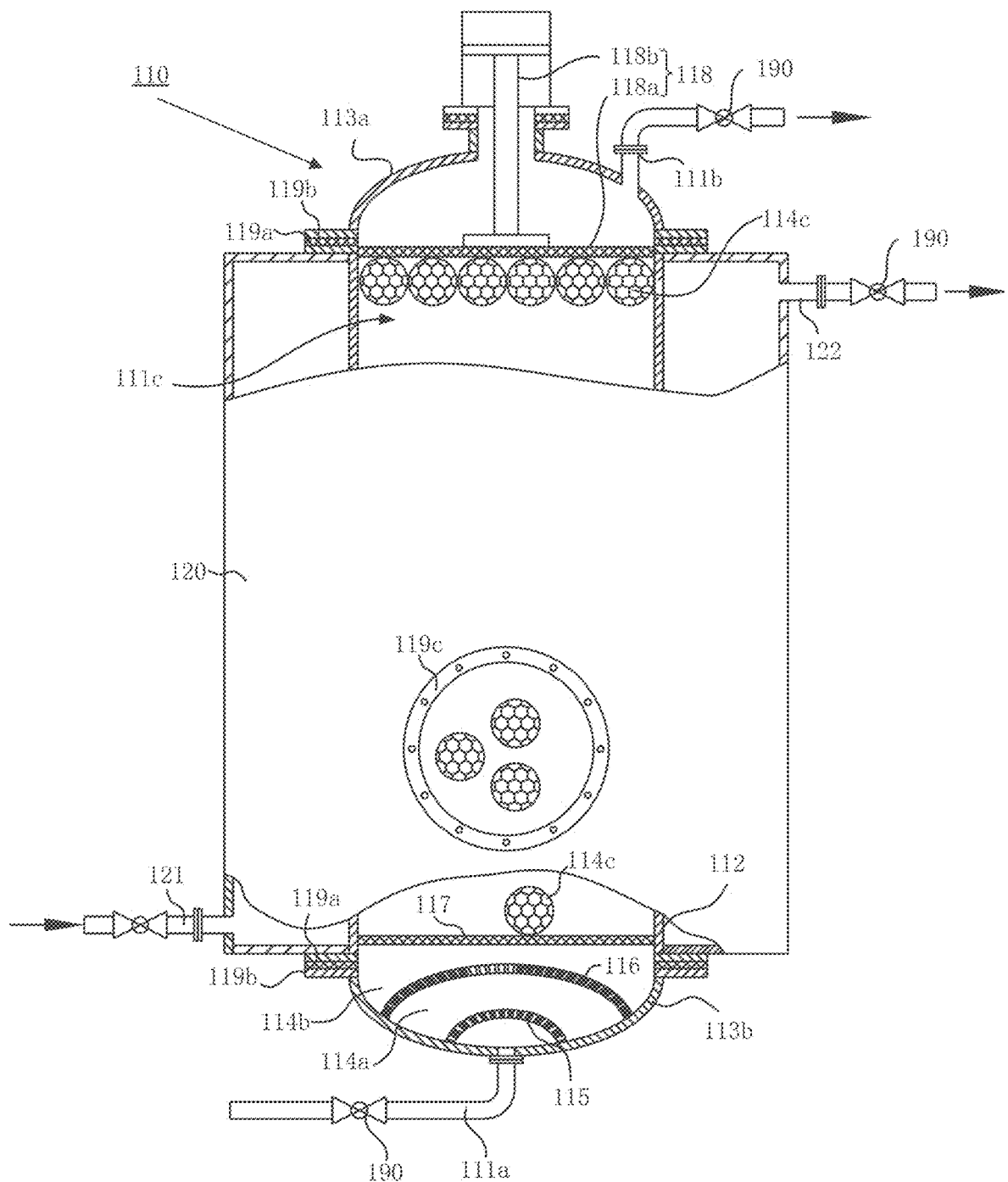
FIG. 2 is a schematic structural diagram of a first thermostatic assembly and a first pressure swing adsorption tower according to an embodiment of the present disclosure.
Figure 3:
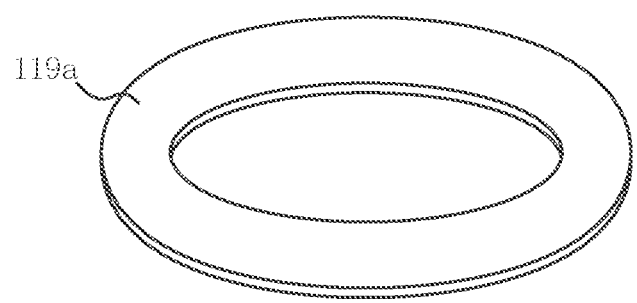
FIG. 3 is a schematic structural diagram of a sealing gasket according to an embodiment of the present disclosure.
Figure 4:
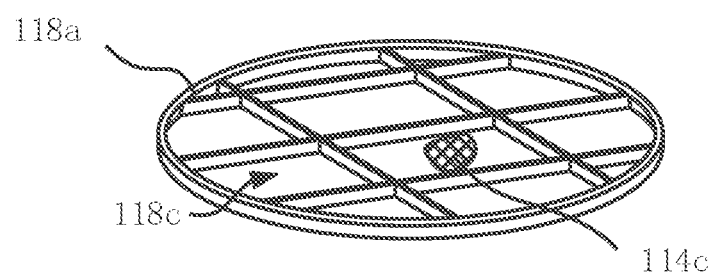
FIG. 4 is a schematic structural diagram of a filler compression grid according to an embodiment of the present disclosure.
Figure 5:
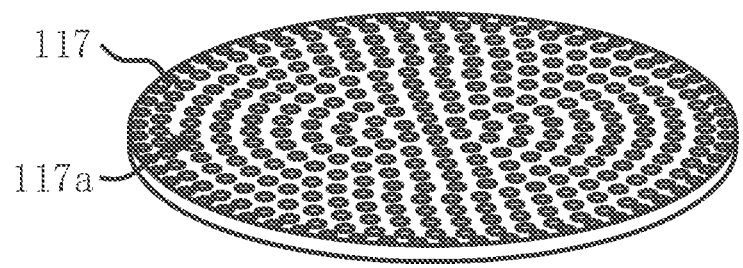
FIG. 5 is a schematic structural diagram of a lower mesh plate according to an embodiment of the present disclosure.
Figure 6:
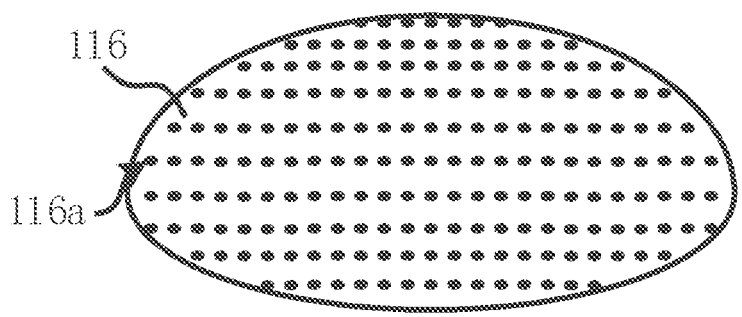
FIG. 6 is a schematic structural diagram of a secondary gas distributor according to an embodiment of the present disclosure.
Figure 7:
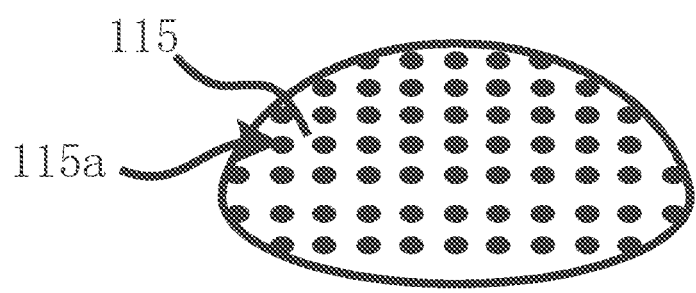
FIG. 7 a schematic structural diagram of a primary gas distributor according to an embodiment of the present disclosure.

Specifically, the first pressure swing adsorption tower 110 is provided with a first accommodating chamber 111c (shown in FIG. 2), a first vent port 111a, and a first exhaust port 111b which are in communication with the first accommodating chamber 111c. The first accommodating chamber 111c is configured to accommodate or hold an adsorption material 114c (shown in FIG. 2). The first pressure swing adsorption tower 110 is at least partially disposed adjacent to the first thermostatic assembly 120. The gas storage tank 130 is provided with a gas inlet/outlet port 131. The first branch pipe 141 couples the first vent port 111a with the gas inlet/outlet port 131, and the second branch pipe 142 is configured to introduce an ethylene oxide waste gas to be treated from an ethylene oxide waste gas source. In some embodiments, the ethylene oxide waste gas to be treated may be output from the ethylene oxide sterilizer 200 into the first pressure swing adsorption tower 110 through the first vent port 111a. In one embodiment, the second branch pipe 142 is in communication with the fourth exhaust port 250 of the ethylene oxide sterilizer 200. In this embodiment, the first vent port 111a is located at the bottom of the first pressure swing adsorption tower 110, and the first exhaust port 111b is located at the top of the first pressure swing adsorption tower 110. However, the embodiments are not limited to this configuration.

The second pressure swing adsorption tower 150 (which may be similar to the first pressure swing adsorption tower 110) is provided with a second accommodating chamber (not shown), and a second vent port 151a and a second exhaust port 151b which are in communication with the second accommodating chamber. The second accommodating chamber is configured to accommodate the adsorption material 114c. The second pressure swing adsorption tower 150 is at least partially disposed adjacent to the second thermostatic assembly 160. The third branch pipe 143 and the fourth branch pipe 144 are in communication with the second vent port 151a. The third branch pipe 143 is configured to communicate the second vent port 151a with the gas inlet/outlet port 131, and the fourth branch pipe 144 is configured to introduce the ethylene oxide waste gas to be treated output from an ethylene oxide waste gas source (which may be the ethylene oxide sterilizer 200) into the second pressure swing adsorption tower 150 through the second vent port 151a. In one embodiment, the fourth branch pipe 144 is in communication with a fourth exhaust port 250 of the ethylene oxide sterilizer 200. In this embodiment, the second vent port 151a is located at the bottom of the second pressure swing adsorption tower 150, and the second exhaust port 151b is located at the top of the second pressure swing adsorption tower 150. However, the embodiments are not limited to this configuration.

In one embodiment, the first pressure swing adsorption tower 110 is at least partially disposed in the first thermostatic assembly 120, and the second pressure swing adsorption tower 150 is at least partially disposed in the second thermostatic assembly 160. The first thermostatic assembly 120 and the second thermostatic assembly 160 can provide the first pressure swing adsorption tower 110 and the second pressure swing adsorption tower 150, respectively, with a lower temperature required during the adsorption process, thereby improving the efficiency of the adsorption treatment. In addition, the vent ports (111a and 151a) and exhaust ports (111b and 151b) of the first pressure swing adsorption tower 110 and the second pressure swing adsorption tower 150 may be respectively connected in parallel through pipes, so that during the operation of the whole device/system 100, the adsorption and desorption processes can be alternately performed by the first pressure swing adsorption tower 110 and the second pressure swing adsorption tower 150, thereby continuously treating the ethylene oxide waste gas and improving the treatment efficiency.

Optionally, the device/system 100 for treating the ethylene oxide waste gas further includes a first main pipe 171 and a second main pipe 172. The first branch pipe 141 and the third branch pipe 143 may be in communication with one end of the first main pipe 171. The other end of the first main pipe 171 may be configured to be in communication with the gas inlet/outlet port 131 of the gas storage tank 130. The second branch pipe 142 and the fourth branch pipe 144 may be in communication with one end of the second main pipe 172, and the other end of the second main pipe 172 may be in communication with the fourth exhaust port 250 of the ethylene oxide sterilizer 200. The first branch pipe 141 and the third branch pipe 143 meet at the first main pipe 171, so that the discharge of the ethylene oxide desorbed with depressurization from the first pressure swing adsorption tower 110 and the second pressure swing adsorption tower 150 to the gas storage tank 130 through the first main pipe 171 can be facilitated, and the incoming ethylene oxide is mixed evenly in the gas storage tank 130. The second branch pipe 142 and the fourth branch pipe 144 meet at the second main pipe 172, so that the ethylene oxide waste gas in the ethylene oxide sterilizer 200 is introduced into the first pressure swing adsorption tower 110 and the second pressure swing adsorption tower 150.

Optionally, the device/system 100 for treating the ethylene oxide waste gas further includes a gas filter 181. The gas filter 181 is disposed on the first main pipe 171. The gas filter 181 is in communication with the first branch pipe 141, the third branch pipe 143, and the gas storage tank 130 through the first main pipe 171. The ethylene oxide desorbed and recovered from the first pressure swing adsorption tower 110 and the second pressure swing adsorption tower 150 can be filtered by the gas filter 181 to remove particles carried over from fillers (e.g., an adsorption material 114c, a water-absorbing material 114a, an oil-absorbing material 114b, etc.), thereby improving the cleanliness of the ethylene oxide recovered in the gas storage tank 130.

Optionally, the device/system 100 for treating the ethylene oxide waste gas further includes a flowmeter 182, a heat exchanger 183, a gas-liquid separator 184, and a gas dryer 185. The flowmeter 182, the heat exchanger 183, the gas-liquid separator 184, and the gas dryer 185 are disposed on the second main pipe 172, and are in communication with each other through the second main pipe 172, and are disposed sequentially along a direction away from the exhaust port of the ethylene oxide sterilizer 200.

The flowmeter 182 is used to detect a flow rate of the gas in the second main pipe 172, so as to facilitate the real-time tracking and monitoring of the gas flow conditions in the second main pipe 172. The heat exchanger 183 can cool the ethylene oxide waste gas (which is at a higher temperature after sterilization), thereby improving the adsorption rate. The gas-liquid separator 184 and the gas dryer 185 can remove the moisture in the waste gas and improve the dryness of the gas, thereby improving the adsorption rate.

Optionally, the device/system 100 for treating the ethylene oxide waste gas further includes a first booster pump 186a, a first vacuum pump 186b, and a second booster pump 186c. The first booster pump 186a is disposed on the first main pipe 171, for example, between the gas filter 181 and the gas storage tank 130. The first booster pump 186a may be able to increase the pressure in the gas storage tank 130 and to increase the amount of gas storage in the gas storage tank 130. The first vacuum pump 186b and the second booster pump 186c are disposed on the second main pipe 172, for example, both are disposed between the gas-liquid separator 184 and the gas dryer 185. The first vacuum pump 186b is used to pump out the ethylene oxide waste gas from the ethylene oxide sterilizer 200. The second booster pump 186c is used to pressurize the waste gas in the second main pipe 172, so as to control the gas pressure in the first pressure swing adsorption tower 110 or the second pressure swing adsorption tower 150, and further increase the adsorption rate of the ethylene oxide in the first pressure swing adsorption tower 110 or the second pressure swing adsorption tower 150. Optionally, both the first booster pump 186a and the second booster pump 186c are pneumatic booster pumps, and the motive gas is nitrogen.

Optionally, the device/system 100 for treating the ethylene oxide waste gas further includes at least one of a first ethylene oxide concentration detector 187a, a second ethylene oxide concentration detector 187b, and a third ethylene oxide concentration detector 187c. The first ethylene oxide concentration detector 187a is provided on the first main pipe 171, for example, between the gas filter 181 and the gas storage tank 130. Further, the device/system 100 for treating the ethylene oxide waste gas further includes a discharge pipe 173, and the first exhaust port 111b and the second exhaust port 151b are both in communication with the discharge pipe 173. The second ethylene oxide concentration detector 187b is provided on the discharge pipe 173. Optionally, the device/system 100 for treating the ethylene oxide waste gas 100 further includes an exhaust pipe 132. The gas inlet/outlet port 131 of the gas storage tank 130 and the other end of the first main pipe 171 are in communication with the exhaust pipe 132. The third ethylene oxide concentration detector 187c is provided on the exhaust pipe 132. The first ethylene oxide concentration detector 187a is used to monitor the concentration of the desorbed and recovered ethylene oxide to monitor the desorption effect and to control the process flow. The second ethylene oxide concentration detector 187b is used to detect the concentration of the ethylene oxide in the first pressure swing adsorption tower 110 and the second pressure swing adsorption tower 150 after adsorption, so as to detect the adsorption effect and control the process flow. The third ethylene oxide concentration detector 187c is used to monitor the average concentration of the ethylene oxide recovered in the gas storage tank 130 for multiple times, so as to facilitate the calculation of process parameters and the implementation of the process flow during the reuse of the recovered ethylene oxide.

Optionally, the first thermostatic assembly 120 is a first thermostatic water tank, which surrounds an outer wall of the first pressure swing adsorption tower 110. The second thermostatic assembly 160 is a second thermostatic water tank, which surrounds an outer wall of the second pressure swing adsorption tower 150. By using the thermostatic water tank as the thermostatic assembly, the rapid cooling of the first pressure swing adsorption tower 110 and the second pressure swing adsorption tower 150 can be achieved, due to the characteristic of large specific heat capacity of water, thereby controlling the temperature level. Further, the first thermostatic water tank is provided with a water inlet port 121 and a water outlet port 122, both of which are in communication with a rainwater collector, respectively. This configuration allows the thermostatic water tank to cool down using the rainwater, and also allows the water after heat transfer to enter the rainwater collector to be mixed with other rainwater that are not subjected to heat transfer to cool down, thereby reducing treatment costs. Optionally, the water inlet port 121 may also be connected to a source of tap water.

In some embodiments, the device/system 100 for treating the ethylene oxide waste gas further includes several valves 190. The first branch pipe 141, the second branch pipe 142, the first exhaust port 111b, the water inlet port 121, the water outlet port 122, the gas inlet/outlet port 131, and the fourth exhaust port 250 are provided with valves 190. The provision of these valves 190 facilitates automatic control, detection and repair, or replacement of parts. In addition, the provision of these valves 190 is also conducive to the realization of a variety of operating processes. For example, pressurizing adsorption and depressurizing desorption are alternately performed by the first pressure swing adsorption tower 110 and the second pressure swing adsorption tower 150, and the corresponding pressurizing adsorption process is accompanied with the cyclic cooling of the first thermostatic assembly 120 or the second thermostatic assembly 160, thereby achieving the continuous treatment of the ethylene oxide waste gas.

As shown in FIGS. 2 to 7, in one embodiment, the first pressure swing adsorption tower 110 includes a first tower body 112, a first upper sealing cover 113a, a first lower sealing cover 113b, a water-absorbing material 114a, an oil-absorbing material 114b, a primary gas distributor 115, a secondary gas distributor 116, a lower mesh plate 117, and a first filler compression assembly 118.

Optionally, the first upper sealing cover 113a and the first lower sealing cover 113b are connected to a top end and a bottom end of the first tower body 112, respectively. The first tower body 112, the first upper sealing cover 113a, and the first lower sealing cover 113b enclose a first accommodating chamber 111c, which is used to accommodate or hold the adsorption material 114c. The upper and lower sealing covers 113a and 113b are provided for easy opening to repair and replace the filling material in the first tower body 112. Optionally, the adsorption material 114c is a 13× molecular sieve and/or a 4A molecular sieve. These two molecular sieve materials can achieve efficient separation of ethylene oxide and nitrogen under a high-pressure condition, and are beneficial to the desorption of ethylene oxide under a low-pressure condition, thereby realizing the recovery and reuse of ethylene oxide.

Further, sealing gaskets 119a may be disposed between the first upper sealing cover 113a and the first tower body 112 and between the first lower sealing cover 113b and the first tower body 112, to prevent gas from escaping the first pressure swing adsorption tower 110. The first upper sealing cover 113a and the first tower body 112, and the first lower sealing cover 113b and the first tower body 112 may also be tightly connected to each other by flanges 119b. Optionally, the first tower body 112 may also be provided with an observation hole 119c which is covered with a transparent sealing plate. The first thermostatic assembly 120 may be disposed adjacent to the first tower body 112 in an area that avoids the observation hole 119c or an observation hole area may be provided in the first thermostatic assembly 120. The provision of the observation hole 119c is convenient for observing the inside of the first pressure swing adsorption tower 110. The observation hole 119c is also convenient for determining when to clean and replace the adsorption material 114c.

Further, the primary gas distributor 115, the water-absorbing material 114a, the secondary gas distributor 116, the oil-absorbing material 114b, and the lower mesh plate 117 are disposed sequentially between the first lower sealing cover 113b and the adsorption material 114c in a direction approaching to the adsorption material 114c. The space between the first lower sealing cover 113b and the adsorption material 114c is filled with the water-absorbing material 114a, which helps to absorb moisture in a mixed ethylene oxide waste gas and prevent water vapor from affecting the adsorption of ethylene oxide. While filling the space between the water-absorbing material 114a and the adsorption material 114c with the oil-absorbing material can absorb the oil contents potentially mixed in the mixed ethylene oxide waste gas, thereby avoiding the pollution of the oil contents to the adsorption material 114c, and prolonging the service life of the adsorption material 114c. The primary gas distributor 115 is provided with a plurality of first holes 115a (shown in FIG. 7) which have a diameter smaller than a particle size of the water-absorbing material 114a. The secondary gas distributor 116 is provided with a plurality of second holes 116a (shown in FIG. 6) which have a diameter smaller than a particle size of the oil-absorbing material. The lower mesh plate 117 is provided with a plurality of third holes 117a (shown in FIG. 5) which have a diameter smaller than a particle size of the adsorption material 114c. The arrangement of the holes on the primary gas distributor 115, the secondary gas distributor 116, and the lower mesh plate 117 and their diameters, is conducive to uniform gas diffusion to the adsorption material 114c on the one hand, and is convenient to respectively carry the adsorption material 114c, the oil-absorbing material 114b, and the water-absorbing material 114a on the other hand, so as to prevent the adsorption material 114c, the oil-absorbing material 114b, and the water-absorbing material 114a from being mixed with each other or falling out of the first pressure swing adsorption tower 110.

Optionally, the first filler compression assembly 118 is connected to the first upper sealing cover 113a and is pressed onto a top end of the adsorption material 114c. The first filler compression assembly 118 compresses the fillers (e.g., an adsorption material 114c, a water-absorbing material 114a, an oil-absorbing material 114b, etc.), which is beneficial to increasing the filling volume and improving the adsorption capacity of ethylene oxide on the one hand, and can compress the adsorption material 114c to prevent the adsorption material 114c from being blown up or worn out on the other hand. The first filler compression assembly 118 includes a filler compression grid 118a and a first filler compression column 118b. The filler compression grid 118a is located in the first accommodating chamber 111c and is pressed onto the top end of the adsorption material 114c. The filler compression grid 118a is provided with a plurality of fourth holes 118c (shown in FIG. 4) which have a diameter smaller than the particle size of the adsorption material 114c. One end of the filler compression column 118b is connected to the filler compression grid 118a passing through the first upper sealing cover 113a, and the filler compression column 118b is capable of compressing the filler compression grid 118a against the adsorption material 114c.

Similarly, the second pressure swing adsorption tower 150 includes a second tower body, a second upper sealing cover, a second lower sealing cover, and a second filler compression assembly. The second pressure swing adsorption tower 150 may also be filled with the water-absorbing material 114a, the oil-absorbing material 114b, the primary gas distributor 115, the secondary gas distributor 116, and the lower mesh plate 117. The connection configuration and mutual relationship of these components are the same as or similar to those of the first pressure swing adsorption tower 110.

In one embodiment, the ethylene oxide sterilizer 200 includes a sterilizer body 210, a gas inlet pipe 220, a second vacuum pump 230, a fourth ethylene oxide concentration detector 240, and a fourth exhaust port 250. The gas inlet pipe 220 is used to introduce ethylene oxide gas, auxiliary nitrogen and, and the like into the sterilizer body 210. The gas inlet pipe 220 may be in communication with the inside of the sterilizer body 210 through both ends of the sterilizer body 210, so as to allow the ethylene oxide in the sterilizer body 210 to be continuously circulated through the gas inlet pipe 220. The second vacuum pump 230 is disposed on the gas inlet pipe 220, and is used to mix ethylene oxide and nitrogen and drive the mixed gas to be circulated in the sterilizer body 210 and the gas inlet pipe 220. The fourth ethylene oxide concentration detector 240 is disposed on the gas inlet pipe 220, and is used to detect the concentration of ethylene oxide entering the sterilizer body 210. The fourth exhaust port 250 may be in communication with the first vent port 111a or the second vent port 151a through the second main pipe 172 to deliver ethylene oxide waste gas into the first pressure swing adsorption tower 110 or the second pressure swing adsorption tower 150.

Taking the first pressure swing adsorption tower 110 as an example, the operation principle is as follows:

The first lower sealing cover 113b and the first tower body 112 are connected and tightly sealed by the flange 119b, and the joint therebetween is filled with the sealing gasket 119a for sealing. The primary gas distributor 115, the water-absorbing material 114a, the secondary gas distributor 116, the oil-absorbing material 114b, and the lower mesh plate 117 are sequentially placed on the first lower sealing cover 113b. The adsorption material 114c is loaded into the first tower body 112, and after the first tower body 112 is filled, the first upper sealing cover 113a and the first tower body 112 are tightly connected by the flange 119b, and the joint therebetween is filled with the sealing gasket 119a for sealing. The adsorption material 114c is compressed and fixed by the filler compression grid 118a and the filler compression column 118b. The primary gas distributor 115, the secondary gas distributor 116, and the lower mesh plate 117 are provided with holes which have diameters smaller than the sizes of the water-absorbing material 114a, the oil-absorbing material 114b, and the adsorption material 114c, respectively, so that the water-absorbing material 114a, the oil-absorbing material 114b, and the adsorption material 114c are prevented from leaking into a lower layer, and the gas can be uniformly dispersed and sequentially enter the water-absorbing material 114a, the oil-absorbing material 114b, and the adsorption material 114c for treatment. The filler compression grid 118a is provided with holes which have a diameter smaller than the size of the adsorption material 114c. The adsorption material 114c is compressed and fixed by the filler compression grid 118a, so that the adsorption material 114c is prevented from being blown up by gas and normal ventilation can be guaranteed. In addition, the internal condition of the first pressure swing adsorption tower 110 can be observed through the observation hole 119c, which facilitates the cleaning and replacement of the adsorption material 114c. During the recovery of the ethylene oxide after pressure swing adsorption, the cooling water can be continuously introduced through the first thermostatic water tank 120 for circulation, so that the first pressure swing adsorption tower 110 can be maintained at a low constant temperature (20° C. to 30° C.) throughout the operation process. Further, since the water used comes from the rainwater collector and/or tap water, the operation is simple and convenient.

After entering the first pressure swing adsorption tower 110, the ethylene oxide waste gas is uniformly dispersed into the water-absorbing material 114a through the primary gas distributor 115 to remove residual water vapor, and after being dried, the ethylene oxide waste gas is uniformly dispersed into the oil-absorbing material 114b through the secondary gas distributor 116 to remove oily substances, and then the ethylene oxide waste gas is uniformly dispersed into the adsorption material 114c through the lower mesh plate 117 to be adsorbed. After the ethylene oxide waste gas is adsorbed by the adsorption material 114c during pressurization, the residual gas is discharged through the first exhaust port 111b through the filler compression grid 118a. The ethylene oxide recovered by depressurizing desorption is discharged into the gas storage tank 130 from the first branch pipe 141 provided at the bottom of the first pressure swing adsorption tower 110.

The operation principle of the second pressure swing adsorption tower 150 is the same as or similar to that of the first pressure swing adsorption tower 110 described above.

The above-mentioned device/system 100 for treating the ethylene oxide waste gas has at least the following advantages:

In the device/system 100 for treating the ethylene oxide waste gas, the ethylene oxide in the ethylene oxide waste gas is adsorbed and recovered by the adsorption material 114c in the first pressure swing adsorption tower 110, which has good recovery effect, safe and simple operation, and has no environmental pollution. Meanwhile, the adsorption material 114c in the pressure swing adsorption tower can be desorbed and regenerated under the condition of specific temperature and pressure, which is conducive to the recovery and reuse of ethylene oxide on the one hand, and is also conducive to the regeneration and reuse of the adsorption material 114c on the other hand.

By using the device/system 100 for treating the ethylene oxide waste gas, when the ethylene oxide waste gas with a concentration of 10% Vol to 50% Vol is recovered after a pressure swing adsorption is performed by the first pressure swing adsorption tower 110 whose internal pressure being pressurized to 0.5 MPa to 0.8 MPa, the maximum recovery concentration reaches 99.99% Vol, the average recovery concentration reaches 12% Vol to 72% Vol, and the recovery efficiency reaches 45% to 65%. When the ethylene oxide waste gas with a concentration of 44% Vol is recovered after a pressure swing adsorption is performed one to four times by the pressure swing adsorption tower 110 whose internal pressure being pressurized to 0.5 MPa, the average recovery concentration reaches 65% Vol to 77% Vol, and the recovery efficiency is 22% to 52%.

An embodiment of the present disclosure further provides a method for treating an ethylene oxide sterilization waste gas performed by the foregoing device/system 100 for treating the ethylene oxide waste gas, including the following steps:

S1: injecting the ethylene oxide waste gas into the first pressure swing adsorption tower 110;

S2: simultaneously cooling the first pressure swing adsorption tower 110 to a first preset temperature by the first thermostatic assembly 120 while increasing a pressure in the first pressure swing adsorption tower 110 to a first preset pressure, and adsorbing ethylene oxide in the ethylene oxide waste gas by the adsorption material 114c in the first pressure swing adsorption tower 110;

S3: stopping cooling of the first pressure swing adsorption tower 110 by the first thermostatic assembly 120, causing the first pressure swing adsorption tower 110 to be in communication with an outside of the first pressure swing adsorption tower 110 through the first exhaust port 111b, and discharging a first gas in the first pressure swing adsorption tower 110 through the first exhaust port 111b, so as to reduce the pressure in the first pressure swing adsorption tower 110 to a second preset pressure;

S4: isolating the first exhaust port 111b from the outside of the first pressure swing adsorption tower 110, causing the first vent port 111a to be in communication with the gas inlet/outlet port 131, and desorbing the ethylene oxide adsorbed by the adsorption material 114c in the first pressure swing adsorption tower 110 to the gas storage tank 130 through the first vent port 111*a* and the gas inlet/outlet port 131, so as to reduce the pressure in the first pressure swing adsorption tower 110 to a third preset pressure.

The step S1 is a waste gas injection step, step S2 is a pressurizing adsorption step, step S3 is a discharging depressurization step, and step S4 is a depressurizing desorption step.

According to the method for treating the ethylene oxide waste gas, the adsorption capacity of the adsorption material 114*c* to absorb different substances may be different under different temperature and pressure conditions, so that the recovery and reuse of ethylene oxide in the ethylene oxide waste gas is achieved, the concentration of ethylene oxide in the discharged waste gas is greatly reduced, and the influence on the external environment and the human health is greatly reduced. The method for treating the ethylene oxide waste gas has the advantages of good recovery effect, safe and simple operation, and environmental protection.

In some embodiments, the first preset temperature is 20° C. to 30° C., the first preset pressure is 0.5 MPa to 0.8 MPa, the second preset pressure is 30% to 60% of the first preset pressure, and the third preset pressure is 0 MPa.

In some embodiments, during the pressurizing adsorption (S2), the first pressure swing adsorption tower 110 is cooled to 20° C. to 30° C. by the first thermostatic assembly 120, and the pressure in the first pressure swing adsorption tower 110 is increased to 0.5 MPa to 0.8 MPa by the second booster pump 186*c*. The adsorption of ethylene oxide is facilitated at the temperature and the pressure, and energy conservation and economy are achieved. When desorption is performed (S4), the first pressure swing adsorption tower 110 is depressurized to 0 MPa, the desorption effect is better, and the energy conservation and economy are achieved.

In an embodiment, prior to the waste gas injection step (S1), the following step is further included: causing the ethylene oxide waste gas output from the ethylene oxide sterilizer 200 to flow sequentially through the heat exchanger 183 for cooling, through the gas-liquid separator 184 for gas-liquid separation, and through the gas dryer 185 for drying. Ethylene oxide waste gas is cooled by flowing through the heat exchanger 183, which can improve the adsorption rate. Then the ethylene oxide waste gas flows through the gas-liquid separator 184 and the gas dryer 185 to remove the moisture in the ethylene oxide waste gas and improve the dryness of the ethylene oxide waste gas, which can also improve the adsorption rate.

Optionally, in the depressurizing desorption step (S4), the ethylene oxide gas desorbed in the first pressure swing adsorption tower 110 flows out through the first vent port 111*a*, and is then filtered by the gas filter 181, then enters the gas storage tank 130 through the gas inlet/outlet port 131. The desorbed and recovered ethylene oxide can be filtered to remove the filler particles (e.g., adsorption material particles, water-absorbing material particles, oil-absorbing material particles, etc.), by passing through the gas filter 181, thereby improving the cleanliness of the ethylene oxide recovered into the gas storage tank 130.

Optionally, at the same time as the discharging depressurization step (S3) is performed, the following steps are further included: monitoring a concentration of ethylene oxide at the first exhaust port 111*b* of the first pressure swing adsorption tower 110 online in real time by the second ethylene oxide concentration detector 187*b*, sampling the gas discharged from the first exhaust port 111*b* of the first pressure swing adsorption tower 110 using a sampling device and a composite membrane gas sampling bag, and detecting a concentration of ethylene oxide in a sample by a gas chromatograph. These steps facilitate the detection of the adsorption effect and the control of the process flow.

At the same time as the depressurizing desorption step is performed (S4), the following steps are further included: monitoring a concentration of ethylene oxide discharged from the gas inlet/outlet port of the gas storage tank 130 online in real time by the third ethylene oxide concentration detector 187*c*, sampling the gas discharged from the gas storage tank 130 using the sampling device and the composite membrane gas sampling bag, and detecting a concentration of ethylene oxide in a sample by the gas chromatograph. These steps facilitate the calculation of process parameters and the implementation of the process flow during the reuse of the recovered ethylene oxide.

In some embodiments, the foregoing method for treating the ethylene oxide waste gas further includes: repeating the steps of waste gas injection (S1), pressurizing adsorption (S2), discharging depressurization (S3), and depressurizing desorption (S4) in sequence for one to three times. New ethylene oxide waste gas is continuously injected into the device/system for treating the ethylene oxide waste gas, and each time new ethylene oxide waste gas is injected into the device/system for treating the ethylene oxide waste gas the foregoing method repeats. The ethylene oxide waste gas may be adsorbed and desorbed several times, which can improve the desorption effect of ethylene oxide.

In one embodiment, the method for treating the ethylene oxide waste gas further includes:

S1': injecting the ethylene oxide waste gas into the second pressure swing adsorption tower 150;

S2': simultaneously cooling the second pressure swing adsorption tower 150 to the first preset temperature by the second thermostatic assembly 160 while, increasing the pressure in the second pressure swing adsorption tower 150 to the first preset pressure, and adsorbing ethylene oxide in the ethylene oxide waste gas by the adsorption material 114*c* in the second pressure swing adsorption tower 150;

S3': stopping cooling the second pressure swing adsorption tower 150 by the second thermostatic assembly 160, causing the second pressure swing adsorption tower 150 to be in communication with an outside of the second pressure swing adsorption tower 150 through the second exhaust port 151*b*, and discharging gas in the second pressure swing adsorption tower 150 through the second exhaust port 151*b*, so as to reduce the pressure in the second pressure swing adsorption tower 150 to the second preset pressure; and S4': isolating the second exhaust port 151*b* from the outside of the second pressure swing adsorption tower 150, causing the second vent port 151*a* to be in communication with the gas inlet/outlet port 131, and desorbing the ethylene oxide adsorbed by the adsorption material 114*c* in the second pressure swing adsorption tower 150 to the gas storage tank 130 through the second vent port 151*a* and the gas inlet/outlet port 131, so as to reduce the pressure in the second pressure swing adsorption tower 150 to the third preset pressure.

Optionally, the method for treating the ethylene oxide waste gas further includes a step of treating the ethylene oxide waste gas by alternately using the first pressure swing adsorption tower 110 and the second pressure swing adsorption tower 150, so that the ethylene oxide waste gas can be continuously introduced into the system 10 for treating the ethylene oxide waste gas for treatment. In one embodiment, the step S2' is performed after the step S2, the step S3' is performed after the step S3, and the step S4' is performed after the step S4.

In one embodiment, after the pressurizing adsorption (S2) in the first pressure swing adsorption tower 110 is completed, pressurizing adsorption (S2') begins to be performed in the second pressure swing adsorption tower 150, and at the same time, discharging depressurization (S3) and depressurizing desorption (S4) begin to be performed in the first pressure swing adsorption tower 110. After the discharging depressurization (S3) and depressurizing desorption (S4) in the first pressure swing adsorption tower 110 is completed, pressurizing adsorption (S2) begins to be performed in the first pressure swing adsorption tower 110 again, and at the same time, discharging depressurization (S3') and depressurizing desorption (S4') begin to be performed in the second pressure swing adsorption tower 150. The above circulation is repeated until all the treatments for the ethylene oxide sterilizing gases are completed.

The pressurizing adsorption (S2 and S2') and depressurizing desorption (S4 and S4') recovery processes are alternately and circularly performed in the first pressure swing adsorption tower 110 and the second pressure swing adsorption tower 150, which ensures the continuous treatment for the ethylene oxide waste gas and improves the treatment efficiency, and is also conducive to ensure the sufficient pressure in the first pressure swing adsorption tower 110 or the second pressure swing adsorption tower 150 during adsorption.

Examples

The ethylene oxide referred to in the examples is industrial ethylene oxide with a purity of 99.99%, the nitrogen is industrial nitrogen with a purity of 99.9%, and the adsorption material 114c is a 13× molecular sieve and a 4A molecular sieve, which are industrial products.

Relevant parameters for detecting the content of ethylene oxide in the ethylene oxide waste gas using a sampling device and a sampling method of a composite membrane gas sampling bag are described as follows:

(1) Gas chromatography detection: sampling detection
Instrument: Gas chromatograph GC2020;
Chromatographic column: Chromosorb101HP60-80 mesh, length 2 m, diameter 3 mm;
Temperature: column temperature 120° C., sample injector 150° C., detector 150° C.;
Carrier gas: nitrogen 35 mL/min, hydrogen 35 mL/min, air 350 mL/min;
Sample Injection: gas sample 1 mL;
Detector: flame ionization detector (FID).

(2) Ethylene oxide concentration detector: online real-time detection of ethylene oxide gas concentration in pipe
Instrument: On-line ethylene oxide concentration detector thermal conductivity MIC-500s-ETO (0 to 99% Vol, resolution 0.01% Vol)
Fixed ethylene oxide detection alarm electrochemistry JSAS-ETO-AX (0 to 100 ppm, resolution 0.01 ppm)
Online ethylene oxide concentration detector PID (0 to 2000 ppm, resolution 0.1 ppm)

Example 1

A method for treating an ethylene oxide waste gas includes the following steps:

(1) Using the above device/system 100 for treating the ethylene oxide waste gas, an ethylene oxide waste gas was injected into the first pressure swing adsorption tower 110 through the first vacuum pump 186b and the second booster pump 186c for adsorption, and an injection flow rate was detected by the flowmeter 182, the ethylene oxide waste gas was cooled by the heat exchanger 183, water and a mixed gas of ethylene oxide were separated by the gas-liquid separator 184, and the mixed gas of ethylene oxide was dried by the gas dryer 185. At the same time, after the first pressure swing adsorption tower 110 was cooled to 20° C. to 30° C. by the first thermostatic assembly 120, and adsorption pressurization was performed to 0.5 MPa to 0.8 MPa, the injection of the ethylene oxide waste gas into the first pressure swing adsorption tower 110 was stopped, and the cooling was also stopped, thus, the pressurizing adsorption was completed. After the pressurizing adsorption in the first pressure swing adsorption tower 110 was completed, the pressurizing adsorption was performed in the second pressure swing adsorption tower 150, and simultaneously, a depressurizing desorption was performed in the first pressure swing adsorption tower 110.

(2) A discharging depressurization was performed in the first pressure swing adsorption tower 110, and residual gas after the pressurizing adsorption was discharged through the first exhaust port 111b, so that the pressure in the first pressure swing adsorption tower 110 was reduced to 30% to 60% of the original pressure. A concentration of ethylene oxide in the discharge pipe 173 was monitored online in real time by the second ethylene oxide concentration detector 187b. At the same time, gas discharged at the first exhaust port 111b was sampled with a sampling device and a composite membrane gas sampling bag, and a concentration of ethylene oxide in the sample was detected by a gas chromatograph. After the depressurizing desorption in the first pressure swing adsorption tower 110 was completed, the pressurizing adsorption was performed in the first pressure swing adsorption tower 110 again. At the same time, the depressurizing desorption was performed in the second pressure swing adsorption tower 150. The pressure swing adsorption and the depressurizing recovery processes were performed alternately in the two pressure swing adsorption towers. That is, the pressurizing adsorption process in the first pressure swing adsorption tower 110 and the depressurizing desorption process in the second pressure swing adsorption tower 150 were performed simultaneously, and the pressurizing adsorption process in the second pressure swing adsorption tower 150 and the depressurizing desorption process in the first pressure swing adsorption tower 110 were performed simultaneously.

(3) The ethylene oxide gas after the depressurizing desorption was discharged through the first vent port 111a and the second vent port 151a, and filtered by the gas filter 181. A concentration of ethylene oxide filtered by the gas filter 181 was monitored online in real time by the first ethylene oxide concentration detector 187a. The filtered ethylene oxide was injected into the gas storage tank 130 through the first booster pump 186a for storage until the pressures of the first pressure swing adsorption tower 110 and the second pressure swing adsorption tower 150 were reduced to 0 MPa, thus, the depressurizing desorption was completed. A concentration of ethylene oxide discharged from the gas storage tank 130 was monitored online in real time by the third ethylene oxide concentration detector 187c. At the same time, the gas discharged from the gas storage tank 130 was sampled with the sampling device and the composite membrane gas sampling bag, and a concentration of ethylene oxide in the sample was detected by the gas chromatograph.

Example 2

(1) The first pressure swing adsorption tower 110 was filled with a 13× molecular sieve and the ethylene oxide sterilizer 200 was evacuated by the second vacuum pump 230. Ethylene oxide and nitrogen were injected through the gas inlet pipe 220 of the ethylene oxide sterilizer 200, mixed circularly by the second vacuum pump 230, monitored by the fourth ethylene oxide concentration detector 240, and sampled by the sampling device and the composite membrane gas sampling bag. The concentrations of ethylene oxide in the ethylene oxide sterilizer 200 were detected by the gas chromatograph reaching 10.12% Vol, 20.35% Vol, 32.14% Vol, and 44.23% Vol, respectively.

(2) Using the above device/system 100 for treating the ethylene oxide waste gas, an ethylene oxide waste gas was injected into the first pressure swing adsorption tower 110 through the first vacuum pump 186*b* and the second booster pump 186*c* for adsorption, and an injection flow rate was detected by the flowmeter 182, the ethylene oxide waste gas was cooled by the heat exchanger 183, water and a mixed gas of ethylene oxide were separated by the gas-liquid separator 184, and the mixed gas of ethylene oxide was dried by the gas dryer 185. At the same time, after the first pressure swing adsorption tower 110 was cooled to 20° C. to 30° C. by the first thermostatic assembly 120, and adsorption pressurization was performed to 0.5 MPa, the injection of the ethylene oxide waste gas into the first pressure swing adsorption tower 110 was stopped, and the cooling was also stopped, thus, the pressurizing adsorption was completed.

(3) A discharging depressurization was performed in the first pressure swing adsorption tower 110 and residual gas after the pressurizing adsorption was discharged through the first exhaust port 111*b*, so that the pressure in the first pressure swing adsorption tower 110 was reduced to 0.2 MPa. A concentration of ethylene oxide in the discharge pipe 173 (i.e., at the first exhaust port 111*b* at this time) was monitored online in real time by the second ethylene oxide concentration detector 187*b*. At the same time, gas discharged at the first exhaust port 111*b* was sampled with a sampling device and a composite membrane gas sampling bag, and a concentration of ethylene oxide in the sample was detected by the gas chromatograph.

(4) The ethylene oxide gas after the depressurizing desorption was discharged through the first vent port 111*a* and the second vent port 151*a*, and filtered by the gas filter 181. A concentration of ethylene oxide filtered by the gas filter 181 was monitored online in real time by the first ethylene oxide concentration detector 187*a*. The filtered ethylene oxide was injected into the gas storage tank 130 through the first booster pump 186*a* for storage until the pressures of the first pressure swing adsorption tower 110 and the second pressure swing adsorption tower 150 were reduced to 0 MPa, thus, the depressurizing desorption was completed. A concentration of ethylene oxide discharged from the gas storage tank 130 was monitored online in real time by the third ethylene oxide concentration detector 187*c*. At the same time, the gas discharged from the gas storage tank 130 was sampled with the sampling device and the composite membrane gas sampling bag, and a concentration of ethylene oxide in the sample was detected by the gas chromatograph.

Figure 8:
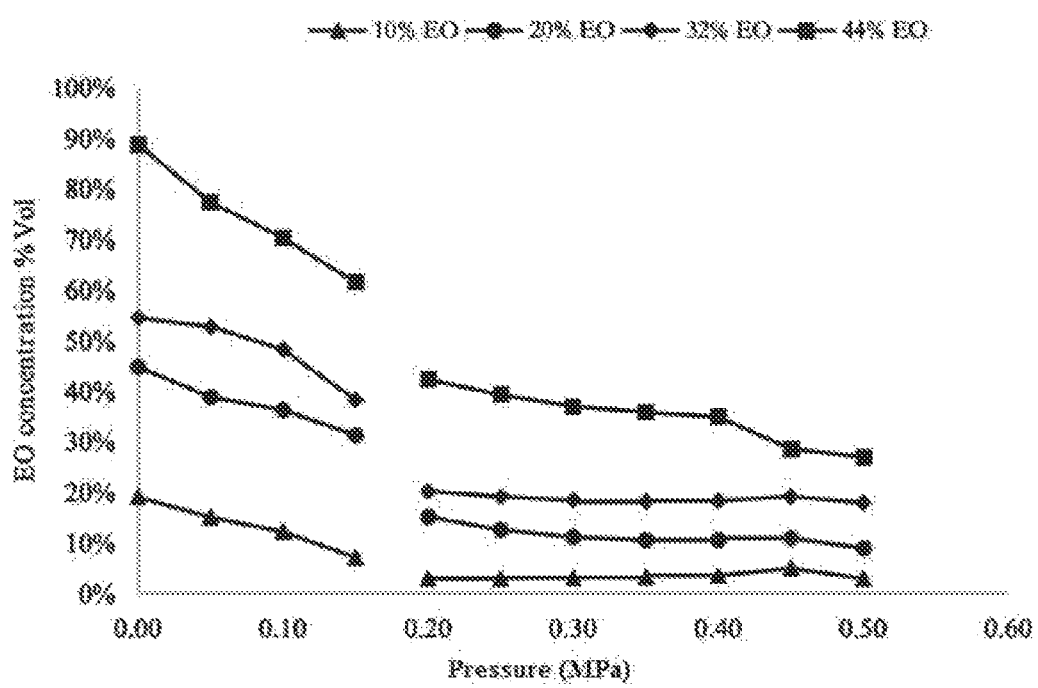
FIG. 8 shows recovery concentrations of ethylene oxide waste gases with different concentrations after pressure swing adsorption by a device/system for treating an ethylene oxide waste gas using a 3× molecular sieve according to an embodiment of the present disclosure.
Figure 9:
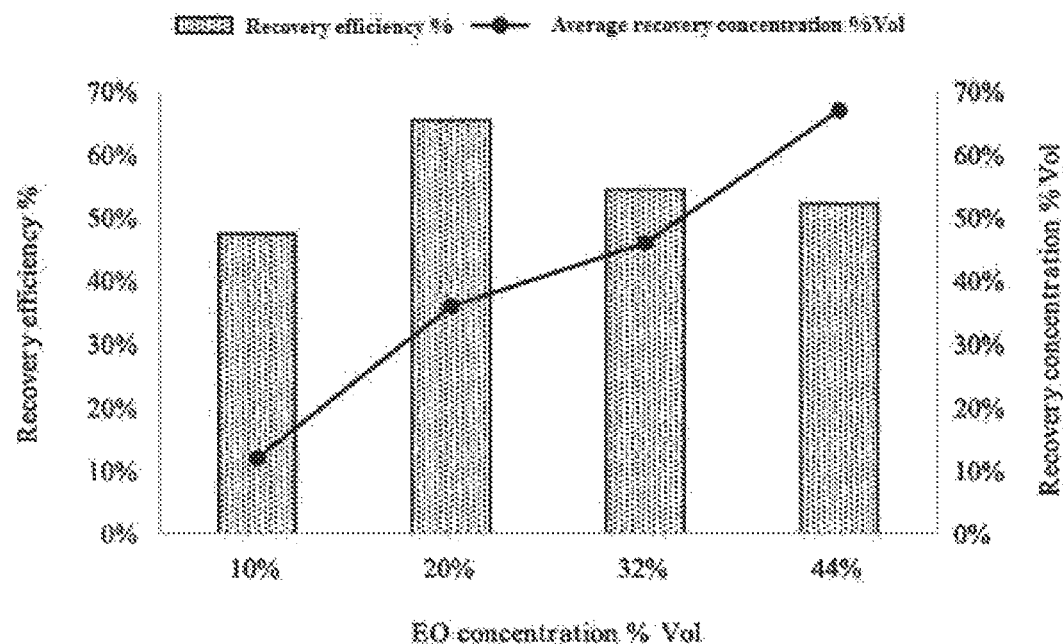
FIG. 9 shows recovery results of ethylene oxide waste gases with different concentrations after pressure swing adsorption by a device/system for treating an ethylene oxide waste gas using a 13× molecular sieve according to an embodiment of the present disclosure.
Figure 10:
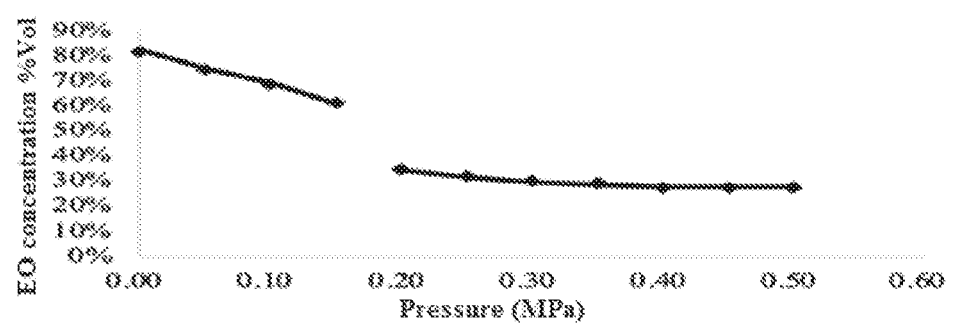
FIG. 10 shows a recovery result of an ethylene oxide gas with a concentration of 44% Vol after adsorption for one time with a pressure swing adsorption tower of a device/system for treating an ethylene oxide waste gas according to an embodiment of the present disclosure.
Figure 11:
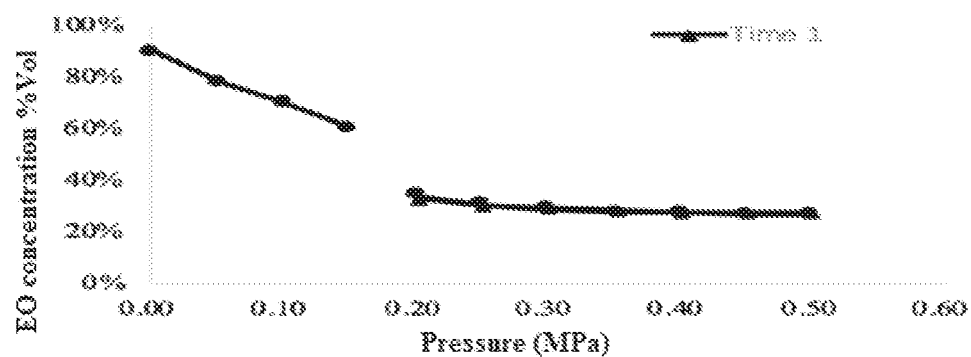
FIG. 11 shows a recovery result of an ethylene oxide waste gas with a concentration of 44% Vol after adsorption for 2 times with a pressure swing adsorption tower of a device/system for treating an ethylene oxide waste gas according to an embodiment of the present disclosure.
Figure 12:
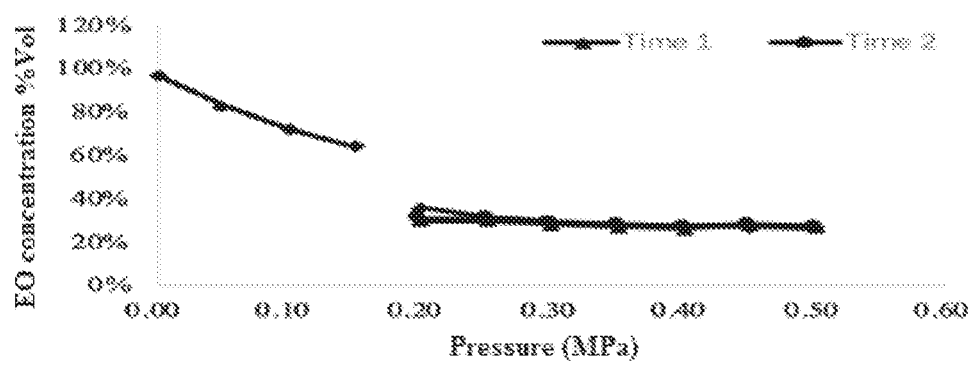
FIG. 12 shows a recovery result of an ethylene oxide waste gas with a concentration of 44% Vol after adsorption for 3 times with a pressure swing adsorption tower of a device/system for treating an ethylene oxide waste gas according to an embodiment of the present disclosure.
Figure 13:
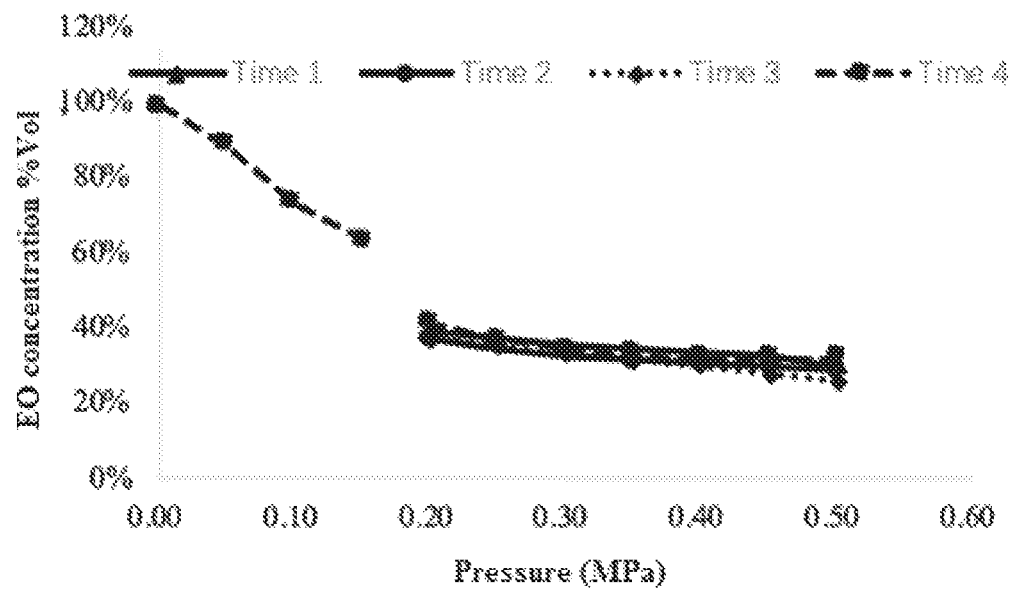
FIG. 13 shows a recovery result of an ethylene oxide waste gas with a concentration of 44% Vol after adsorption for 4 times with a pressure swing adsorption tower of a device/system for treating an ethylene oxide waste gas according to an embodiment of the present disclosure.

FIG. 8 shows real-time concentrations of ethylene oxide in the gas under different pressures monitored online by the second ethylene oxide concentration detector 187*b* during a depressurizing recovery process after pressure swing adsorption for ethylene oxide waste gases with different concentrations using a 13× molecular sieve. It can be seen that, after the ethylene oxide waste gases with a concentration of 10.12% Vol, 20.35% Vol, 32.14% Vol, and 44.23% Vol were respectively pressurized to 0.5 MPa for pressure swing adsorption treatment, and in a process of discharging the gases from the top for depressurization (from 0.5 MPa to 0.2 MPa), the concentration of ethylene oxide in the discharged gas was lower, and the curve was relatively flat. In a process of recovering the residual gas from the bottom (0.2 MPa to 0.0 MPa) after the pressure was reduced to 0.2 MPa, the concentration of ethylene oxide recovered was significantly increased. As shown in FIG. 9, as detected by gas chromatography, the concentrations of ethylene oxide in the discharged gases after pressure swing adsorption were about 3.10% Vol, 11.45% Vol, 19.22% Vol, and 29.34% Vol, respectively; the average concentrations of ethylene oxide in the recovered gases were 12.44% Vol, 36.32% Vol, 46.15% Vol, and 67.33% Vol, respectively, and the recovery efficiencies were 47.24%, 64.78%, 53.82%, and 52.13%, respectively.

Example 3

(1) The first pressure swing adsorption tower 110 was filled with a 13X molecular sieve and the ethylene oxide sterilizer 200 was evacuated by the second vacuum pump 230. Ethylene oxide and nitrogen were injected through the gas inlet pipe 220 of the ethylene oxide sterilizer 200, mixed circularly by the second vacuum pump 230, monitored by the fourth ethylene oxide concentration detector 240, and sampled by the sampling device and the composite membrane gas sampling bag. The concentrations of ethylene oxide in the ethylene oxide sterilizer 200 were detected by the gas chromatograph, reaching 44.23% Vol.

(2) Using the above device/system 100 for treating the ethylene oxide waste gas, an ethylene oxide waste gas was injected into the first pressure swing adsorption tower 110 through the first vacuum pump 186*b* and the second booster pump 186*c* for adsorption, and an injection flow rate was detected by the flowmeter 182, the ethylene oxide waste gas was cooled by the heat exchanger 183, water and a mixed gas of ethylene oxide were separated by the gas-liquid separator 184, and the mixed gas of ethylene oxide was dried by the gas dryer 185. At the same time, after the first pressure swing adsorption tower 110 was cooled to 20° C. to 30° C. by the first thermostatic assembly 120, and adsorption pressurization was performed to 0.5 MPa, the injection of the ethylene oxide waste gas into the first pressure swing adsorption tower 110 was stopped, and the cooling was also stopped, thus, the pressurizing adsorption was completed.

(3) A discharging depressurization was performed in the first pressure swing adsorption tower 110 and residual gas after the pressurizing adsorption was discharged through the first exhaust port 111*b*, so that the pressure in the first pressure swing adsorption tower 110 was reduced to 0.2 MPa. A concentration of ethylene oxide at the first exhaust port 111*b* was monitored online in real time by the second ethylene oxide concentration detector 187*b*. At the same time, gas discharged at the first exhaust port 111*b* was sampled with a sampling device and a composite membrane gas sampling bag, and a concentration of ethylene oxide in the sample was detected by the gas chromatograph.

(4) The steps (2) to (3) were repeated 1 to 3 times. In other words, the mixed gas in the ethylene oxide sterilizer 200 was injected into the first pressure swing adsorption tower 110 until the pressure increased to 0.5 MPa, and the adsorption was performed 1 to 3 times.

(5) The ethylene oxide gas after the depressurizing desorption was discharged through the first vent port 111*a* and the second vent port 151*a*, and filtered by the gas filter 181. A concentration of ethylene oxide filtered by the gas filter 181 was monitored online in real time by the first ethylene oxide concentration detector 187a. The filtered ethylene oxide was injected into the gas storage tank 130 through the first booster pump 186a for storage until the pressures of the first pressure swing adsorption tower 110 and the second pressure swing adsorption tower 150 were reduced to 0 MPa, thus, the depressurizing desorption was completed. A concentration of ethylene oxide discharged from the gas storage tank 130 was monitored online in real time by the third ethylene oxide concentration detector 187c. At the same time, the gas discharged from the gas storage tank 130 was sampled with the sampling device and the composite membrane gas sampling bag, and a concentration of ethylene oxide in the sample was detected by the gas chromatograph.

Recovery results of Example 3 are shown in FIGS. 10 to 13. Using 13× molecular sieve as the adsorbent, the ethylene oxide waste gas with a concentration of 44.23% Vol was injected into the first pressure swing adsorption tower 110 until the pressure increased to 0.5 MPa, and was recovered after 1 to 4 times of adsorption. In a process of discharging the gases from the top for depressurization (from 0.5 MPa to 0.2 MPa), the real-time concentrations of ethylene oxide in the gas under different pressures monitored online by the first ethylene oxide concentration detector 187a were lower, and the curve was relatively flat. In a process of recovering the residual gas from the bottom (0.2 MPa to 0.0 MPa) after the pressure was reduced to 0.2 MPa, the concentration of ethylene oxide recovered was significantly increased. As detected by gas chromatography, the discharge concentrations after 1 to 4 times of pressure swing adsorptions were about 29.14% Vol, 28.65% Vol, 29.26% Vol, and 33.05% Vol, respectively; the average concentrations of ethylene oxide in the recovered gases were 67.33% Vol, 65.75% Vol, 76.28% Vol, and 77.47% Vol, respectively, and the recovery efficiencies were 51.56%, 42.81%, 27.43%, 22.52%, respectively.

Example 4

(1) The first pressure swing adsorption tower was filled with a 4A molecular sieve and the ethylene oxide sterilizer 200 was evacuated by the second vacuum pump 230. Ethylene oxide and nitrogen were injected through the gas inlet pipe 220 of the ethylene oxide sterilizer 200, mixed circularly by the second vacuum pump 230, monitored by the fourth ethylene oxide concentration detector 240, and sampled by the sampling device and the composite membrane gas sampling bag. The concentrations of ethylene oxide in the ethylene oxide sterilizer 200 were detected by the gas chromatograph, reaching 10.34% Vol, 20.54% Vol, 30.10% Vol, and 40.56% Vol, respectively.

(2) Using the above device/system 100 for treating the ethylene oxide waste gas, an ethylene oxide waste gas was injected into the first pressure swing adsorption tower 110 through the first vacuum pump 186b and the second booster pump 186c for adsorption, and an injection flow rate was detected by the flowmeter 182, the ethylene oxide waste gas was cooled by the heat exchanger 183, water and a mixed gas of ethylene oxide were separated by the gas-liquid separator 184, and the mixed gas of ethylene oxide was dried by the gas dryer 185. At the same time, after the first pressure swing adsorption tower 110 was cooled to 20° C. to 30° C. by the first thermostatic assembly 120, and adsorption pressurization was performed to 0.5 MPa, the injection of the ethylene oxide waste gas into the first pressure swing adsorption tower 110 was stopped, and the cooling was also stopped, thus, the pressurizing adsorption was completed.

(3) A discharging depressurization was performed in the first pressure swing adsorption tower 110, and residual gas after the pressurizing adsorption was discharged through the first exhaust port 111b, so that the pressure in the first pressure swing adsorption tower 110 was reduced to 0.2 MPa. A concentration of ethylene oxide at the first exhaust port 111b was monitored online in real time by the second ethylene oxide concentration detector 187b. At the same time, gas discharged at the first exhaust port 111b was sampled with a sampling device and a composite membrane gas sampling bag, and a concentration of ethylene oxide in the sample was detected by the gas chromatograph.

(4) The steps (2) to (3) were repeated for 1 to 3 times. In other words, the mixed gas in the ethylene oxide sterilizer 200 was injected into the first pressure swing adsorption tower 110 until the pressure in the first pressure swing adsorption tower 110 increased to 0.5 MPa, and the adsorption was performed for 1 to 3 times.

(5) The ethylene oxide gas after the depressurizing desorption was discharged through the first vent port 111a and the second vent port 151a, and filtered by the gas filter 181. A concentration of ethylene oxide filtered by the gas filter 181 was monitored online in real time by the first ethylene oxide concentration detector 187a. The filtered ethylene oxide was injected into the gas storage tank 130 through the first booster pump 186a for storage until the pressures of the first pressure swing adsorption tower 110 and the second pressure swing adsorption tower 150 were reduced to 0 MPa, thus, the depressurizing desorption was completed. A concentration of ethylene oxide discharged from the gas storage tank 130 was monitored online in real time by the third ethylene oxide concentration detector 187c. At the same time, the gas discharged from the gas storage tank 130 was sampled with the sampling device and the composite membrane gas sampling bag, and a concentration of ethylene oxide in the sample was detected by the gas chromatograph.

Figure 14:
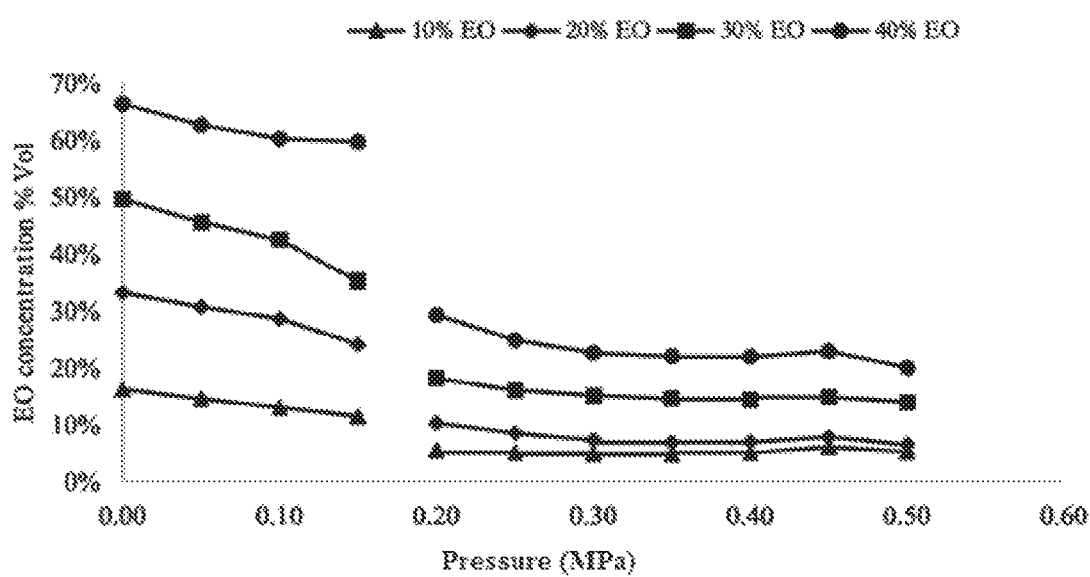
FIG. 14 shows adsorption recovery concentrations of ethylene oxide waste gases with different concentrations after pressure swing adsorption by a device/system for treating an ethylene oxide waste using a 4A molecular sieve according to an embodiment of the present disclosure.
Figure 15:
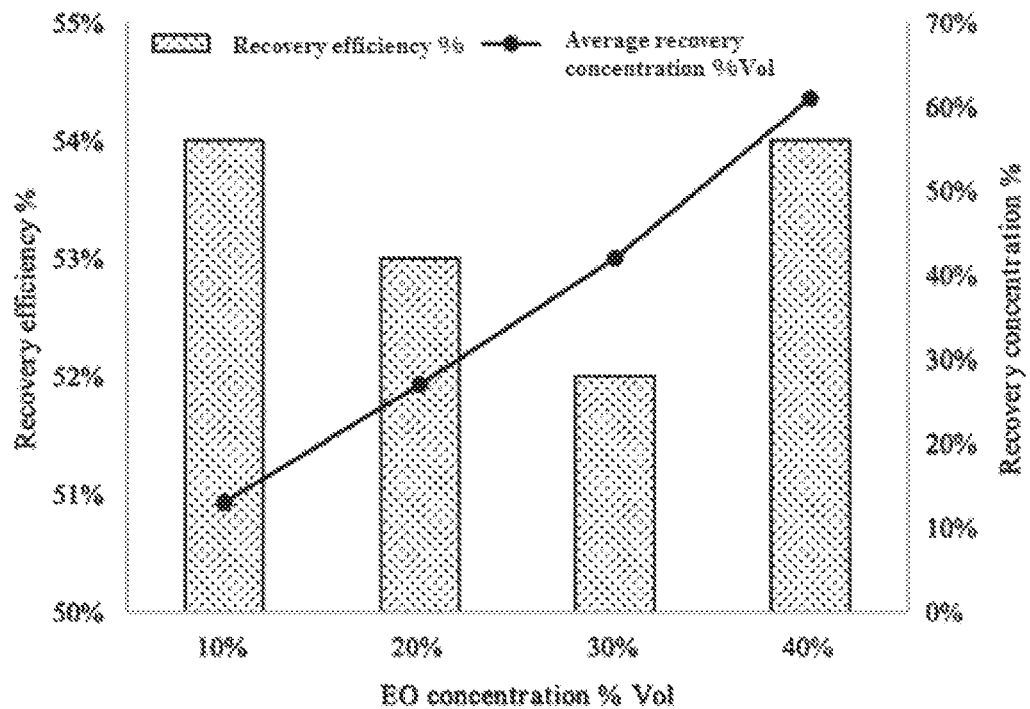
FIG. 15 shows adsorption recovery efficiencies of ethylene oxide waste gases with different concentrations after a pressure swing adsorption by a device/system for treating an ethylene oxide waste gas using a 4A molecular sieve according to an embodiment of the present disclosure.

FIG. 14 shows real-time concentrations of ethylene oxide in the gas monitored online by the second ethylene oxide concentration detector 187b under different pressures during a depressurizing recovery process after the pressure swing adsorption for ethylene oxide waste gases with different concentrations using a 4A molecular sieve. It can be seen that, after the ethylene oxide waste gases with a concentration of 10.34% Vol, 20.54% Vol, 30.10% Vol, and 40.56% Vol were respectively pressurized to 0.5 MPa for the pressure swing adsorption treatment, and in a process of discharging the gases from the top for depressurization (from 0.5 MPa to 0.2 MPa), the concentration of ethylene oxide in the discharged gas was lower, and the curve was relatively flat. In a process of recovering the residual gas from the bottom (0.2 MPa to 0.0 MPa) after the pressure was reduced to 0.2 MPa, the concentration of ethylene oxide recovered was significantly increased. As shown in FIG. 15, as detected by gas chromatography, the average concentrations of ethylene oxide in the recovered gases after the pressure swing adsorption were 13.46% Vol, 27.55% Vol, 42.68% Vol, and 61.49% Vol, respectively, and the recovery efficiencies were 54.06%, 53.33%, 52.65%, and 54.13%, respectively. The pressure swing adsorption effect is similar to the results of the 13× molecular sieve.

Example 5

(1) The first pressure swing adsorption tower 110 and the second pressure swing adsorption tower 150 were filled with a 4A molecular sieve and the ethylene oxide sterilizer 200 was evacuated by the second vacuum pump 230. Ethylene oxide and nitrogen were injected through the gas inlet pipe 220 of the ethylene oxide sterilizer 200, mixed circularly by the second vacuum pump 230, monitored by the fourth ethylene oxide concentration detector 240, and sampled by the sampling device and the composite membrane gas sampling bag. The concentrations of ethylene oxide in the ethylene oxide sterilizer 200 were detected by the gas chromatograph, reaching 40.56% Vol.

(2) Using the above device/system 100 for treating the ethylene oxide waste gas, an ethylene oxide waste gas was injected into the first pressure swing adsorption tower 110 through the first vacuum pump 186*b* and the second booster pump 186*c* for adsorption, and an injection flow rate was detected by the flowmeter 182, the ethylene oxide waste gas was cooled by the heat exchanger 183, water and a mixed gas of ethylene oxide were separated by the gas-liquid separator 184, and the mixed gas of ethylene oxide was dried by the gas dryer 185. At the same time, after the first pressure swing adsorption tower 110 was cooled to 20° C. to 30° C. by the first thermostatic assembly 120, and adsorption pressurization was performed to 0.6 MPa and 0.8 MPa, respectively, the injection of the ethylene oxide waste gas into the first pressure swing adsorption tower 110 was stopped, and the cooling was also stopped, thus, the pressurizing adsorption was completed.

(3) A discharging depressurization was performed in the first pressure swing adsorption tower 110, and residual gas after the pressurizing adsorption was discharged through the first exhaust port 111*b*, so that the pressure in the first pressure swing adsorption tower 110 was reduced to 0.3 MPa. A concentration of ethylene oxide at the first exhaust port 111*b* was monitored online in real time by the second ethylene oxide concentration detector 187*b*. At the same time, gas discharged at the first exhaust port 111*b* was sampled with a sampling device and a composite membrane gas sampling bag, and a concentration of ethylene oxide in the sample was detected by the gas chromatograph.

(4) The ethylene oxide gas after the depressurizing desorption was discharged through the first vent port 111*a* and the second vent port 151*a*, and filtered by the gas filter 181. A concentration of ethylene oxide filtered by the gas filter 181 was monitored online in real time by the first ethylene oxide concentration detector 187*a*. The filtered ethylene oxide was injected into the gas storage tank 130 through the first booster pump 186*a* for storage until the pressures of the first pressure swing adsorption tower 110 and the second pressure swing adsorption tower 150 were reduced to 0 MPa, thus, the depressurizing desorption was completed. A concentration of ethylene oxide discharged from the gas storage tank 130 was monitored online in real time by the third ethylene oxide concentration detector 187*c*. At the same time, the gas discharged from the gas storage tank 130 was sampled with the sampling device and the composite membrane gas sampling bag, and a concentration of ethylene oxide in the sample was detected by the gas chromatograph.

Figure 16:
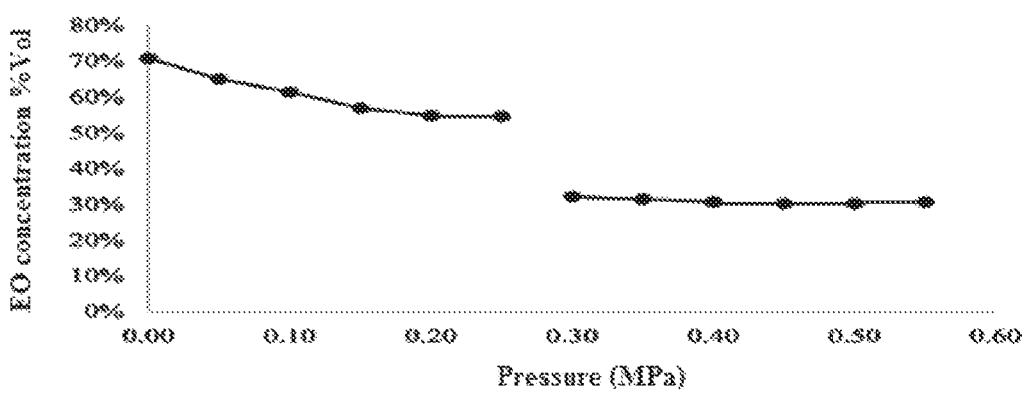
FIG. 16 shows adsorption recovery concentrations of ethylene oxide waste gas after a pressure swing adsorption pressurized to 0.6 MPa by a device/system for treating an ethylene oxide waste gas using a 4A molecular sieve according to an embodiment of the present disclosure.
Figure 17:
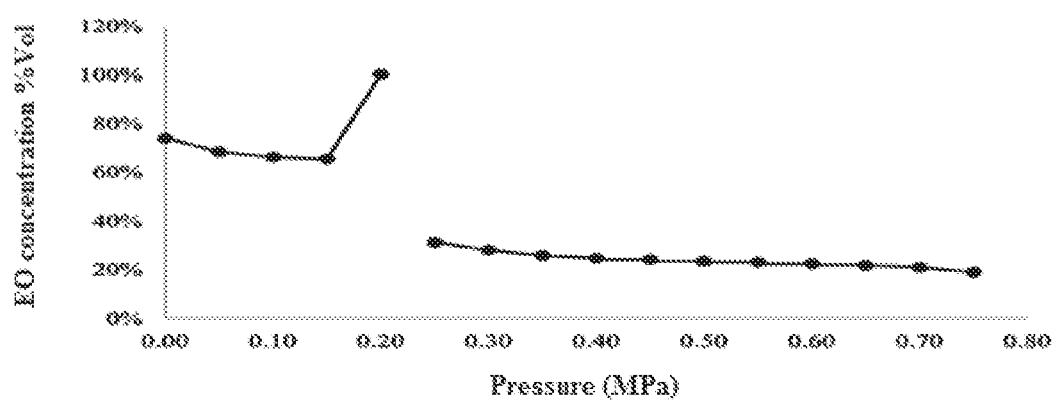
FIG. 17 shows adsorption and recovery concentrations of ethylene oxide waste gas after a pressure swing adsorption pressurized to 0.8 MPa by a device/system for treating an ethylene oxide waste gas using a 4A molecular sieve according to an embodiment of the present disclosure.

FIGS. 16 and 17 show the real-time concentration of ethylene oxide monitored online by the second ethylene oxide concentration detector 187*b* under different pressures, during the pressure swing adsorption for the ethylene oxide waste gas with a concentration of 40.56% Vol using the 4A molecular sieve until the pressure increased to 0.6 MPa and 0.8 MPa and during the depressurizing process. It can be seen from FIG. 16 that, in a process of discharging the gases from the top for depressurization (from 0.6 MPa to 0.3 MPa), the concentration of ethylene oxide in the discharged gas was lower, and the curve was relatively flat. In a process of recovering the residual gas from the bottom (0.3 MPa to 0.0 MPa) after the pressure was reduced to 0.3 MPa, the concentration of ethylene oxide recovered was significantly increased. As detected by gas chromatography, the average concentration of ethylene oxide in the discharged gas was 30.42% Vol, the average concentrations of the recovered ethylene oxide reached 61.59% Vol, and the recovery efficiency reached 45.33%. It can be seen from FIG. 17 that, in a process of discharging the gases from the top for depressurization (from 0.8 MPa to 0.2 MPa), the concentration of ethylene oxide in the discharged gas was lower, and the curve was relatively flat. In a process of recovering the residual gas from the bottom (0.2 MPa to 0.0 MPa) after the pressure was reduced to 0.2 MPa, the concentration of ethylene oxide recovered was significantly increased. As detected by gas chromatography, the average concentration of ethylene oxide in the discharged gas was 25.21% Vol, the average concentrations of the recovered ethylene oxide reached 72.81% Vol, and the recovery efficiency reached 53.24%. In addition, during the recovery process, the ethylene oxide was compressed into liquid at 0.8 MPa, i.e., a pure ethylene oxide, whose concentration monitored by the third ethylene oxide concentration detector 187*c* reached 99.99%. At this time, the pressure remained unchanged, and when the recovery of the pure ethylene oxide was completed, the pressure began to drop, and the concentration also began to decrease.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method for treating an ethylene oxide waste gas comprising:
   injecting the ethylene oxide waste gas into a first pressure swing adsorption tower, wherein injecting the ethylene oxide waste gas into the first pressure swing adsorption tower comprises injecting the ethylene oxide waste gas through a water-absorbing material and an oil-absorbing material before injecting the ethylene oxide waste gas into a first adsorption material, wherein the oil-absorbing material is between the water-absorbing material and the first adsorption material;
   simultaneously cooling the first pressure swing adsorption tower to a first preset temperature by a first thermostatic assembly while increasing a first pressure in the first pressure swing adsorption tower to a first preset pressure;
   adsorbing ethylene oxide in the ethylene oxide waste gas by the first adsorption material in the first pressure swing adsorption tower;
   stopping cooling of the first pressure swing adsorption tower by the first thermostatic assembly while stopping increase of the first pressure in the first pressure swing adsorption tower;
   causing the first pressure swing adsorption tower to be in communication with an outside of the first pressure swing adsorption tower through a first exhaust port of the first pressure swing adsorption tower;
   discharging a first gas in the first pressure swing adsorption tower through the first exhaust port to reduce the first pressure in the first pressure swing adsorption tower to a second preset pressure;
   isolating the first exhaust port from the outside of the first pressure swing adsorption tower;
   causing a first vent port of the first pressure swing adsorption tower to be in communication with a gas inlet/outlet port of a gas storage tank; and
   desorbing the ethylene oxide adsorbed by the first adsorption material in the first pressure swing adsorption tower to the gas storage tank through the first vent port and the gas inlet/outlet port to reduce the first pressure in the first pressure swing adsorption tower to a third preset pressure.

2. The method for treating the ethylene oxide waste gas according to claim 1, wherein the first preset temperature is 20° C. to 30° C., the first preset pressure is 0.5 MPa to 0.8 MPa, the second preset pressure is 30% to 60% of the first preset pressure, and the third preset pressure is 0 MPa.

3. The method for treating the ethylene oxide waste gas according to claim 1, wherein prior to injecting the ethylene oxide waste gas into the first pressure swing adsorption tower, the method further comprises:
   causing the ethylene oxide waste gas to flow sequentially through a heat exchanger for cooling, through a gas-liquid separator for gas-liquid separation, and through a gas dryer for drying.

4. The method for treating the ethylene oxide waste gas according to claim 1, wherein desorbed ethylene oxide flows out through the first vent port, is filtered by a gas filter, and then enters the gas storage tank through the gas inlet/outlet port.

5. The method for treating the ethylene oxide waste gas according to claim 1, further comprising:
   at the same time as stopping cooling of the first pressure swing adsorption tower by the first thermostatic assembly, causing the first pressure swing adsorption tower to be in communication with an outside of the first pressure swing adsorption tower through the first exhaust port, discharging the first gas in the first pressure swing adsorption tower through the first exhaust port to reduce the first pressure in the first pressure swing adsorption tower to the second preset pressure, and monitoring a first concentration of ethylene oxide at the first exhaust port of the first pressure swing adsorption tower in real time by a second ethylene oxide concentration detector; and
   at the same time as isolating the first exhaust port from the outside of the first pressure swing adsorption tower, causing the first vent port to be in communication with the gas inlet/outlet port, desorbing the ethylene oxide adsorbed by the first adsorption material in the first pressure swing adsorption tower to the gas storage tank through the first vent port and the gas inlet/outlet port to reduce the first pressure in the first pressure swing adsorption tower to the third preset pressure, and monitoring a second concentration of ethylene oxide discharged from the gas inlet/outlet port of the gas storage tank in real time by a third ethylene oxide concentration detector.

6. The method for treating the ethylene oxide waste gas according to claim 1, further comprising repeating the method 1 to 3 times, each time with new ethylene oxide waste gas being injected into the first pressure swing adsorption tower.

7. The method for treating the ethylene oxide waste gas according to claim 1, further comprising:
   injecting the ethylene oxide waste gas into a second pressure swing adsorption tower;
   simultaneously cooling the second pressure swing adsorption tower to the first preset temperature by a second thermostatic assembly while increasing a second pressure in the second pressure swing adsorption tower to the first preset pressure;
   adsorbing the ethylene oxide in the ethylene oxide waste gas by a second adsorption material in the second pressure swing adsorption tower;
   stopping cooling of the second pressure swing adsorption tower by the second thermostatic assembly;
   causing the second pressure swing adsorption tower to be in communication with an outside of the second pressure swing adsorption tower through a second exhaust port of the second pressure swing adsorption tower;
   discharging a second gas in the second pressure swing adsorption tower through the second exhaust port to reduce the second pressure in the second pressure swing adsorption tower to the second preset pressure;
   isolating the second exhaust port from the outside of the second pressure swing adsorption tower;
   causing a second vent port of the second swing adsorption tower to be in communication with the gas inlet/outlet port of the gas storage tank; and
   desorbing the ethylene oxide adsorbed by the second adsorption material in the second pressure swing adsorption tower to the gas storage tank through the second vent port and the gas inlet/outlet port to reduce the second pressure in the second pressure swing adsorption tower to the third preset pressure.

8. The method for treating the ethylene oxide waste gas according to claim 1, wherein the first pressure swing adsorption tower comprises a filler compression grid pressed onto a top end of the first adsorption material, and wherein the filler compression grid prevents the first adsorption material from being discharged through the first exhaust port of the first pressure swing adsorption tower.

9. The method for treating the ethylene oxide waste gas according to claim 8, wherein the first pressure swing adsorption tower further comprises a compression column 5 that presses the filler compression grid onto the top end of the first adsorption material.

\* \* \* \* \*